(12) United States Patent
Shimizu et al.

(10) Patent No.: US 8,951,450 B2
(45) Date of Patent: Feb. 10, 2015

(54) APPARATUS AND METHOD FOR PRODUCTION OF LIPOSOMES

(75) Inventors: Yoshitaka Shimizu, Kanagawa (JP);
Yuichiro Satoh, Kanagawa (JP);
Yasuhiko Mibe, Kanagawa (JP);
Masakazu Kuroda, Shiga (JP);
Yuichiro Tsuda, Shiga (JP)

(73) Assignees: Biomedcore, Inc., Kanagawa (JP);
Toray Engineering Co., Ltd., Tokyo (JP)

( * ) Notice: Subject to any disclaimer, the term of this patent is extended or adjusted under 35 U.S.C. 154(b) by 0 days.

(21) Appl. No.: 13/393,598

(22) PCT Filed: Aug. 24, 2010

(86) PCT No.: PCT/JP2010/064239
§ 371 (c)(1),
(2), (4) Date: May 14, 2012

(87) PCT Pub. No.: WO2011/027684
PCT Pub. Date: Mar. 10, 2011

(65) Prior Publication Data
US 2012/0267809 A1   Oct. 25, 2012

(30) Foreign Application Priority Data

Sep. 2, 2009   (JP) ................................. 2009-203054
Jun. 24, 2010  (JP) ................................. 2010-144231

(51) Int. Cl.
*B01J 13/02*  (2006.01)
*B01J 13/20*  (2006.01)
(Continued)

(52) U.S. Cl.
CPC ............... *B01J 13/04* (2013.01); *A61K 9/1277* (2013.01)

USPC .................................................. 264/4.1; 425/5

(58) Field of Classification Search
CPC .................................. B01J 13/02; B01J 13/20
See application file for complete search history.

(56) References Cited

U.S. PATENT DOCUMENTS

| 5,000,887 A | 3/1991 | Tenzel et al. |
| 5,004,611 A | 4/1991 | Leigh |

(Continued)

FOREIGN PATENT DOCUMENTS

| JP | 60-153938 | 8/1985 |
| JP | 03-181415 | 8/1991 |

(Continued)

OTHER PUBLICATIONS

PCT Search Report prepared for PCT/JP2010/064239, mailed Oct. 5, 2010.

(Continued)

*Primary Examiner* — Randy Gulakowski
*Assistant Examiner* — Jeffrey Washville
(74) *Attorney, Agent, or Firm* — Barnes & Thornburg LLP

(57) ABSTRACT

Disclosed are: an apparatus which enables the easy production of liposomes having uniform particle diameters; and others. Specifically disclosed is a liposome production apparatus comprising: a microtube having a flow path through which a lipid-dissolved solution comprising at least one lipid, water and a water-miscible organic solvent can pass; a housing section in which the microtube is accommodated; and a cooling means for cooling the dissolved solution contained in the microtube in the housing section to a temperature at which liposomes can be produced. The apparatus enables the production of liposomes having uniform particle diameters.

9 Claims, 8 Drawing Sheets

(51) Int. Cl.
*B01J 13/04* (2006.01)
*A61K 9/127* (2006.01)

(56) References Cited

U.S. PATENT DOCUMENTS

| | | | |
|---|---|---|---|
| 5,389,523 | A | 2/1995 | Plant et al. |
| 5,772,929 | A | 6/1998 | Enomura et al. |
| 5,776,488 | A | 7/1998 | Mori et al. |
| 6,066,331 | A | 5/2000 | Barenholz et al. |
| 6,331,314 | B1 | 12/2001 | Klinksiek et al. |
| 6,818,227 | B1 | 11/2004 | Uster et al. |
| 2001/0003580 | A1 | 6/2001 | Hui et al. |
| 2002/0160039 | A1 | 10/2002 | Boni et al. |
| 2005/0175683 | A1 | 8/2005 | Zhang |
| 2011/0250262 | A1 | 10/2011 | Shimizu et al. |

FOREIGN PATENT DOCUMENTS

| | | |
|---|---|---|
| JP | 3181415 | 8/1991 |
| JP | 6509547 | 10/1994 |
| JP | 07-53661 | 6/1995 |
| JP | 07-277956 | 10/1995 |
| JP | 2537186 | 7/1996 |
| JP | 9-24269 | 1/1997 |
| JP | 11-139961 | 5/1999 |
| JP | 2002-509102 | 3/2002 |
| JP | 2002509121 | 3/2002 |
| JP | 2002536316 | 10/2002 |
| JP | 2006517594 | 7/2006 |
| JP | 2006-273812 | 10/2006 |
| JP | 2008-255109 | 10/2008 |
| WO | WO86/00238 | 1/1986 |
| WO | WO92/11842 | 7/1992 |
| WO | WO99/36056 | 7/1999 |
| WO | WO99/36104 | 7/1999 |
| WO | WO00/45791 | 8/2000 |
| WO | WO 02/081739 | 10/2002 |
| WO | WO2004/071466 | 8/2004 |

OTHER PUBLICATIONS

Bangham, et al., "Negative Staining of Phospholipids and their Structural Modification by Surface-Active Agents as Observed in the Electron Microscope", 1964, J. Mol. Biology, No. 8, pp. 660-668.

Bangham, et al., "Diffusion of Univalent Ions Across the Lameallae of Swollen Phospholipids", 1965, J. Mol. Biology, No. 13, pp. 238-252.

APPARATUS AND METHOD FOR PRODUCTION OF LIPOSOMES

CROSS-REFERENCE TO RELATED APPLICATIONS

This application is a U.S. national counterpart application of PCT International Application Serial No. PCT/JP2010/064239, filed Aug. 24, 2010, which claims priority to Japanese Patent Application Serial No. 2009-203054 having a filing date of 2 Sep. 2009 and Japanese Patent Application Serial No. 2010-144231 having a filing date of 24 Jun. 2010, all of which are incorporated herein in their entireties by this reference.

TECHNICAL FIELD

The present invention relates to an apparatus and a method for producing liposomes.

BACKGROUND ART

A liposome is a roughly spherical hollow particle enclosed by at least one lipid bilayer composed of lipid molecules. The lipid molecule possesses hydrophilic groups having hydrophilicity and, on the opposite side, lipophilic groups having lipophilicity. For this reason, in contact with water, the molecules form a bilayer, which becomes spherical so that the surface area is minimal, the hydrophilic groups facing outside the bilayer as well as inward toward the inner compartment formed by the bilayer, while the lipophilic groups pointing toward the interior of the bilayer. Since the bilayer thus forming a liposome is similar to the cell membrane constituting the living body, it is easily accepted in the biological environment. In recent years, by taking advantage of this property, liposomes have been a focus of attention as pharmaceutical vesicles in the drug delivery system (DDS), in which a drug encapsulated in the region surrounded by the bilayer is transported to the site in the living body requiring the medicine.

Various techniques have been known as the methods for producing liposomes, of which one typical technique is the Bangham method (thin-film method). In this method, a suspension containing liposomes is obtained as follows: at least one phospholipid is dissolved in an organic solvent, such as chloroform, in a vessel, such as a flask; then by evaporating off chloroform, lipid membrane is temporarily formed at the bottom of the vessel, to which an aqueous solution, such as buffer, is added and the vessel is mixed (A. D. Bangham et al., J. Mol. Biol., 13, 238-252 (1965); A. D. Bangham and R. W. Horne, J. Mol. Biol., 8, 660-668 (1964).

Alternatively, typical industrial manufacturing methods for liposomes include the technique in which lipid components, such as phospholipid dissolved in a water-miscible organic solvent, is added to an aqueous solution by infusion with stirring. The water-miscible organic solvents which can be suitably used here include alcohols, such as methanol, ethanol, isopropyl alcohol, and butanol. It should be noted, however, that the lipid solution should be added to and mixed with an aqueous solution while being warmed so that the dissolved state of the lipid is maintained; this requires precise control of temperature, adding speed or stirring speed (National Publication of International Patent Application No. 2006-517594). Furthermore, another method of producing a preliposome using t-butanol has also been reported (Japanese Translation of International Patent Application No. 1994-509547) This method has an advantage that lipid can be sterilized by filtration and be freeze-dried, since lipid can be maintained as a solution around room temperature by using, as a dissolution solvent of lipid, t-butanol having a water content as low as about 20%.

SUMMARY OF INVENTION

Technical Problem

Unfortunately, the above-mentioned conventional methods for producing liposomes have the following disadvantages: Diameters of liposomes are not uniform, or liposomes having uniform diameters are difficult to be produced. Though liposomes having small diameters (small unilamellar vesicles: SUVs) and liposomes having large diameters (large unilamellar vesicles: LUVs) are both useful, a mixture thereof has a low utility value. PTL 1 discloses a method where water is added to a solution of a lipid in t-butanol (100% concentration) while maintaining the water and the solution, for example, at 35° C. The lipid solution is diluted by being mixed with water, and thereby the t-butanol is also diluted. As a result, the amount of the lipid dissolved in the solution decreases, resulting in separation of the lipid. During the process of mixing, the lipid concentration and the t-butanol concentration in the aqueous solution change from moment to moment, and thereby the reaction does not progress uniformly. As a result, it is difficult to produce liposomes having uniform diameters. A broad particle-size distribution of liposomes can be narrowed using an appropriate pore size filter, in the process of producing the liposomes. However, employment of such a process causes a problem of a reduction in yield of liposomes having a specific desired particle-size distribution. Furthermore, the area to be sterilized for subjecting liposomes to such a process is extended, resulting in an increase in the manufacturing cost.

The present invention has been achieved in view of the above-described disadvantages, and it is an object of the present invention to provide an apparatus and a method that can easily produce liposomes having uniform diameters.

Solution to Problem

The present inventors have diligently studied in order to achieve the above-mentioned objects and, as a result, have found that liposomes having uniform diameters can be produced using the apparatus shown in FIG. 1 by heating a mixture containing one or more lipids, water, and a water-miscible organic solvent to dissolve the lipid or lipids in an aqueous solution containing the water and the water-miscible organic solvent, maintaining the solution in which the lipid or lipids are dissolved at a temperature that is higher than a liposome-forming temperature, more specifically, 40° C. or higher, but is lower than the heating temperature, for a predetermined period of time, and then cooling the solution to a predetermined temperature. Thus, the present invention has been accomplished.

The present invention relates to the following aspects:
(1) A liposome-producing apparatus including a dissolving zone for heating a mixture of one or more lipids and an aqueous solution containing a water-miscible organic solvent to dissolve the lipid or lipids in the aqueous solution, and a first cooling zone being located in the downstream side of the dissolving zone in the solution sending direction for cooling the solution from the dissolving zone to a temperature that is lower than the temperature of the dissolving zone and that allows formation of liposomes;
(2) The liposome-producing apparatus according to the aspect (1), further including a second cooling zone located on the downstream side of the first cooling zone in the solution sending direction and cooling the solution from the first cooling zone to a temperature lower than the temperature of the first cooling zone;

(3) The liposome-producing apparatus according to the aspect (1) or (2), wherein the dissolving zone and the first cooling zone each have a solution sending channel in which a solution flows, and the solution sending channel of the dissolving zone and the solution sending channel of the first cooling zone are connected to each other, and liposomes are formed when the solution is continuously sent from the solution sending channel of the dissolving zone to the solution sending channel of the first cooling zone;

(4) The liposome-producing apparatus according to the aspect (3), wherein the solution sending channels are each sufficiently thin so that the temperature of the solution is maintained approximately uniform in a radial direction of the solution sending channel and the temperatures of the thin channels are maintained constant over the longitudinal direction of the channels;

(5) The liposome-producing apparatus according to the aspect (3) or (4), wherein the solution sending channels each have an inner diameter that allows generation of a turbulent flow of the solution flowing inside the solution sending channel;

(6) The liposome-producing apparatus according to any one of the aspects (1) to (5), wherein at least one of the solution sending channels of the dissolving zone and the first cooling zone is equipped with a sterilization filter;

(7) The liposome-producing apparatus according to any one of the aspects (1) to (6), the apparatus further including a preliposome-forming device for forming liposomes by heating a mixture of one or more lipids and an aqueous solution containing a water-miscible organic solvent to dissolve the lipid or lipids in the aqueous solution and cooling the resulting solution to a temperature lower than the dissolving temperature, wherein the preliposome-forming device is located on the upstream side of the dissolving zone in the solution sending direction, and the dissolving zone heats the solution to dissolve the liposomes in the aqueous solution;

(8) The liposome-producing apparatus according to any one of the aspects (1) to (7), the apparatus further including an encapsulation material feeder located on the upstream side of the dissolving zone in the solution sending direction for mixing a material to be encapsulated inside liposomes with the mixture in the dissolving zone; and (9) The liposome-producing apparatus according to any one of the aspects (1) to (8), wherein the apparatus is connected to an ultrafiltration device on the downstream side than the first cooling zone for concentrating the solution containing the liposomes by removing at least the water-miscible organic solvent from the solution.

The present invention further relates to the following aspects:

(10) A liposome-producing apparatus including a microtube having a channel in which a lipid solution containing one or more lipids, water, and a water-miscible organic solvent flows, a housing for housing the microtube, and a cooling unit for cooling the solution in the microtube in the housing to a liposome-forming temperature;

(11) The liposome-producing apparatus according to the aspect (10), the apparatus further including a dissolving zone for preparing the solution by heating a mixture containing one or more lipids, water, and a water-miscible organic solvent to dissolve the lipid or lipids in an aqueous solution containing the water and the water-miscible organic solvent;

(12) The liposome-producing apparatus according to the aspect (11), wherein the dissolving zone includes a microtube having a channel in which the mixture flows, and the microtube of the dissolving zone and the microtube in the housing are connected to each other;

(13) The liposome-producing apparatus according to the aspect (11) or (12), the apparatus further including a preliposome-forming device for forming liposomes by heating the mixture, before heating the mixture at the dissolving zone, to dissolve the lipid or lipids in the aqueous solution and then cooling the resulting solution to a temperature lower than the dissolving temperature;

(14) The liposome-producing apparatus according to any one of the aspects (10) to (13), the apparatus further including an encapsulation material feeder for supplying both the lipid solution and a material to be encapsulated inside liposomes to the microtube in the housing;

(15) The liposome-producing apparatus according to any one of the aspects (10) to (14), the apparatus further including a cooling zone for further cooling the solution containing the liposomes formed by cooling with the cooling unit;

(16) The liposome-producing apparatus according to any one of the aspects (10) to (15), the apparatus further including a sterilization means for sterilizing the solution; and

(17) The liposome-producing apparatus according to any one of the aspects (10) to (16), the apparatus further including an ultrafiltration device for concentrating the solution containing the liposomes formed by cooling with the cooling unit by removing at least the water-miscible organic solvent from the solution.

The present invention further relates to the following.

(18) A method of producing liposomes, including the steps of: heating a mixture containing one or more lipids, water, and a water-miscible organic solvent to a temperature in a range of 62° C. to 80° C.; maintaining the mixture after the heating step at a temperature of 40° C. or higher but lower than the heating temperature for a predetermined period of time; and cooling the mixture after the maintaining step, wherein the volume of the water-miscible organic solvent is 5 to 30 vol % of the total volume of the aqueous solution containing the water and the water-miscible organic solvent.

The present invention further relates to the following.

(19) A liposome-producing apparatus including:

a preliposome-forming device for forming liposomes by heating a mixture containing one or more lipids, water, and a water-miscible organic solvent to dissolve the lipid or lipids in the aqueous solution and cooling the resulting solution to a temperature lower than the dissolving temperature;

an encapsulation material feeder for mixing a material to be encapsulated inside liposomes with a mixture containing the liposomes formed in the preliposome-forming device;

a dissolving zone for preparing the solution containing the material to be encapsulated by heating the mixture prepared in the encapsulation material feeder to dissolve the lipid or lipids in the mixture in the aqueous solution in the mixture;

a sterilization means for sterilizing the prepared solution before cooling by the cooling unit through the microtube;

a cooling zone for cooling the solution containing the liposomes formed by cooling with the cooling unit; and an ultrafiltration device for concentrating the solution containing the liposomes by removing at least the water-miscible organic solvent from the solution, wherein the dissolving zone includes a microtube having a channel in which the mixture flows; and the microtube of the dissolving zone and the microtube in the housing are connected to each other.

Advantageous Effects of Invention

According to the present invention, liposomes having uniform diameters can be easily produced.

DESCRIPTION OF EMBODIMENTS

Embodiments of the present invention will be described in detail with reference to the drawings.

Figure 1:
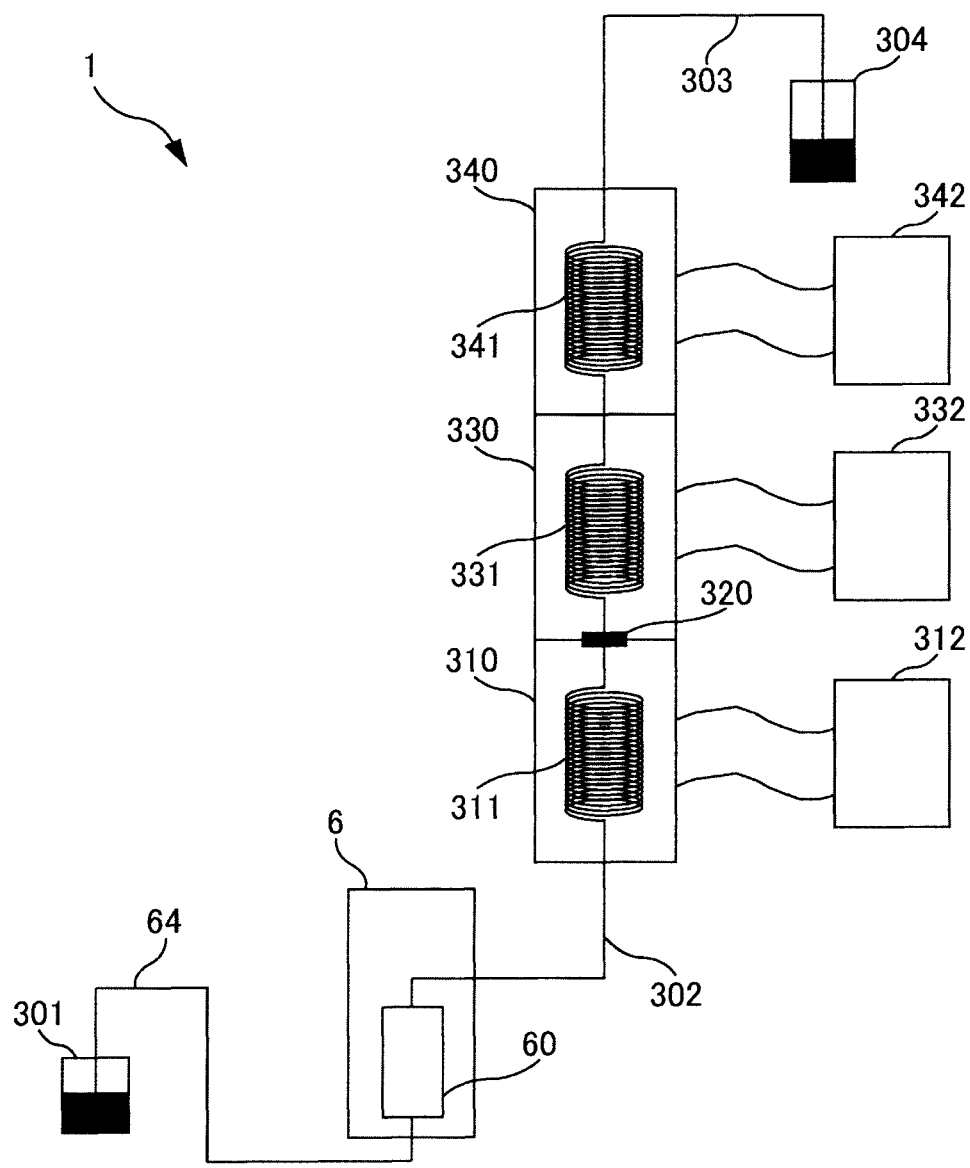
FIG. 1 is a schematic diagram illustrating the construction of a liposome-producing apparatus according to an embodiment of the present invention.

FIG. 1 is a schematic diagram illustrating the construction of a liposome-producing apparatus, which will be described as an embodiment of the present invention.

The liposome-producing apparatus 1 includes a lipid-dissolving tank (dissolving zone) 310, a sterilization filter 320, a liposome-forming tank (first cooling zone) 330, a cooling tank (second cooling zone) 340, and thermostatic baths 312, 332, and 342.

The lipid-dissolving tank 310 is a tank for preparing a solution by heating a mixture supplied from a container 301 by a solution-sending portion 60 of a pump 6 through microtubes 64 and 302 to dissolve one or more lipids in the mixture in an aqueous solution containing water and a water-miscible organic solvent in the mixture. The lipid-dissolving tank 310 is a container having thermal insulation. The lipid-dissolving tank 310 is equipped with a microtube 311. The tank is filled with a heat medium, and the heat medium heats the mixture in the microtube 311. The heat medium in the tank is maintained at a predetermined temperature (temperature in a range of 62° C. to 80° C.) by a thermostatic bath 312 so that the lipid or lipids are dissolved in the aqueous solution containing water and a water-miscible organic solvent. Examples of the thermostatic bath 312 include, but not limited to, a circulating thermostatic bath cycling a heat medium between the lipid-dissolving tank 310 and the thermostatic bath 312. The microtube 311 has, for example, a coiled shape. The heat medium may be a gas or a liquid.

The sterilization filter 320 removes microorganisms such as bacteria in a fluid flowing in channels of microtubes 64, 302, 303, 311, 331, and 341. The sterilization filter 320 may be disposed at any position of the microtubes 64, 302, 303, 311, 331, and 341 between the container 301 and a liposome-collecting container 304, but is preferably disposed between a portion where a lipid solution is prepared and a portion where liposomes are formed, from the viewpoint of sterilization efficiency. Accordingly, in this embodiment, the sterilization filter 320 is disposed at the connection of the lipid-dissolving tank 310 and the liposome-forming tank 330 and sterilizes the lipid solution prepared in the lipid-dissolving tank 310.

The liposome-forming tank 330 is a container having thermal insulation. The liposome-forming tank 330 is a tank for forming liposomes by cooling the lipid solution that has passed through the sterilization filter 320 to a temperature allowing formation of liposomes (40° C. or higher but lower than the temperature of the heat medium in the lipid-dissolving tank 310). The liposome-forming tank 330 is equipped with a microtube 331 having a predetermined length. The liposome-forming tank 330 is filled with a heat medium. The heat medium cools and maintains the lipid solution in the microtube 331 at a predetermined temperature. The heat medium in the tank is maintained at the liposome-forming temperature, by a thermostatic bath 332. Examples of the thermostatic bath 332 include, but not limited to, a circulating thermostatic bath cycling a heat medium between the lipid-dissolving tank 330 and the thermostatic bath 332. The microtube 331 has, for example, a coiled shape. The heat medium (coolant) may be a gas or a liquid.

The microtube 331 may be detachable from the liposome-forming tank 330 so that the microtube 331 can be replaced by one having a different length. Alternatively, the liposome-forming tank 330 may be composed of two or more tanks so that a lipid solution can be sequentially cooled at different temperatures. In the liposome-forming tank 330 composed of two or more tanks, the temperature of the heat medium in each tank is maintained in the range allowing formation of liposomes by a circulating thermostatic bath equipped to each tank.

The cooling tank 340 is a container having thermal insulation. The cooling tank 340 is a tank for cooling the solution containing liposomes formed in the liposome-forming tank 330. The cooling tank 340 is equipped with a microtube 341. The cooling tank 340 is filled with a heat medium, and the heat medium cools the solution in the microtube 341. The heat medium is maintained at a predetermined temperature (higher than 0° C. but lower than the temperature of the heat medium in the liposome-forming tank 330), by a thermostatic bath 342. Examples of the thermostatic bath 342 include, but not limited to, a circulating thermostatic bath cycling a heat medium between the cooling tank 340 and the thermostatic bath 342. The microtube 341 has, for example, a coiled shape. The heat medium may be a gas or a liquid. The thus-formed liposomes are collected into the liposome-collecting container 304 through a microtube 303.

As described above, the liposome-producing apparatus 1 including the thermostatic bath 332 and the liposome-forming tank 330 housing the microtube 331 having a channel in which a lipid solution flows can maintain the lipid solution at the liposome-forming temperature for a predetermined period of time. Consequently, liposomes having uniform diameters can be easily produced.

In addition, the liposome-producing apparatus 1 including the thermostatic bath 312 and the lipid-dissolving tank 310 housing the microtube 311 having a channel in which a mixture containing, for example, one or more lipids, water, and a water-miscible organic solvent flows, can prepare a lipid solution from the mixture. Consequently, liposomes having uniform diameters can be more efficiently produced.

Furthermore, the liposome-producing apparatus 1 including the thermostatic bath 342 and the cooling tank 340 housing the microtube 341 having a channel in which a solution containing liposomes formed in the liposome-forming tank 330 flows can stably produce liposomes having uniform diameters.

In this embodiment, a liposome-producing apparatus 1 including a lipid-dissolving tank 310, a sterilization filter 320, a liposome-forming tank 330, a cooling tank 340, and thermostatic baths 312, 332, and 342 has been described. In the case of injecting a lipid solution prepared in advance, instead of the mixture, into the container 301, the liposome-producing apparatus 1 may not be equipped with the lipid-dissolving tank 310, the thermostatic bath 312, etc. In the case of pouring a mixture or a lipid solution sterilized in advance into the container 301, the liposome-producing apparatus 1 may not be equipped with the sterilization filter 320. In the case of naturally cooling a solution containing liposomes formed in the liposome-forming tank 330, the liposome-producing apparatus 1 may not be equipped with the cooling tank 340, the thermostatic bath 342, etc.

In this embodiment, the solution containing liposomes formed in the liposome-forming tank 330 is collected into the liposome-collecting container 304. Alternatively, the solution may be concentrated by removing the water-miscible organic solvent in the solution with an ultrafiltration device. In the case of forming liposomes encapsulating a material, an ultrafiltration device that can also remove the material being not encapsulated in the liposomes is preferably used.

Furthermore, in this embodiment, the mixture supplied from the container 301 is heated in the lipid-dissolving tank 310 to dissolve the lipid or lipids. Alternatively, a prelipo-some-forming device described below may be located on the upstream side of the lipid-dissolving tank 310, for heating a mixture to dissolve the lipid or lipids in the mixture in the aqueous solution in the mixture and cooling the solution to a temperature lower than the dissolving temperature to form liposomes, before heating the mixture in the lipid-dissolving tank 310.

The material to be encapsulated in liposomes may be mixed in the mixture in advance. The liposome-producing apparatus 1 may be equipped with an encapsulation material feeder for mixing an encapsulation material with a mixture supplied to the lipid-dissolving tank 310 or mixing an encapsulation material with a lipid solution supplied to the liposome-forming tank 330. The encapsulation material feeder is, for example, a pump for supplying an encapsulation material. The encapsulation material is mixed with the mixture or the lipid solution by the encapsulation material feeder through a microtube connected to the microtube 64, 302, or 311.

The microtubes may be made of any material having good thermal conductivity, such as Teflon or stainless steel. The microtubes preferably have an inner diameter within a range of 1.0 to 3.0 mm.

Liposomes to be produced in accordance with the present invention include empty liposomes which contain no physiologically active substance such as a pharmaceutical agent in their vesicle, and liposomes encapsulating physiologically active substances in the vesicle. Liposomes are generally classified as vesicles with relatively small particles (small unilamellar vesicles: SUVs) formed by a single lipid bilayer and vesicles with relatively large particles formed by a single lipid bilayer (large unilamellar vesicles: LUVs) as well as vesicles formed by multiple membrane layers (multi-lamellar vesicles: MLVs). In this embodiment, liposomes having large population of MLV can be produced. Liposomes may be of any particle size, but preferred mean particle diameter is 50 to 2000 nm, and particularly preferred is 100 to 700 nm. The term "particle diameter" as used herein refers to the diameter of a particle measured by dynamic light scattering. The preferred polydispersity index (PDI) is 0.3 or less.

As for the physiologically active substances that can be encapsulated in the liposome, various pharmaceutical agents, cosmetics, and the like can be adopted. Such substances are exemplified by one or a combination of anticancer agents such as cisplatin, 5-fluorouracil, etc. as well as antioxidants, antibacterial agents, anti-inflammatory agents, blood circulation-promoting agents, anti-aging agents, hormone formulation, vitamin formulation, hemoglobin, DNA, RNA, peptides, protein, vaccines, hair-growing agents, moisturizers, coloring agents, whitening agents, pigments, saline, water, etc. However, the physiologically active substances are not limited to the above examples. Moreover, the surface of the liposome may be modified with a functional group or the like. Such modification with a functional group can be realized either by binding a functional group to the phospholipid or the like before or after liposome formation.

Examples of the lipids include soybean lecithin, hydrogenated soybean lecithin, egg yolk lecithin, phosphatidylcholines, phosphatidylserines phosphatidylethanolamines, phosphatidyl inositols, sphingomyelins, phosphatidic acids, long-chain alkyl phosphates, gangliosides, glycolipids, phosphatidyl glycerols, and cholesterols. Phosphatidylcholines can be exemplified by dimyristoylphosphatidylcholine, dipalmitoylphosphatidylcholine, distearoyl phosphatidylcholine, etc. Phosphatidylserines can be exemplified by dipalmitoyl phosphatidylserine, dipalmitoyl phosphatidylserine (sodium salt), phosphatidylserine (sodium salt) derived from bovine brain, etc. Phosphatidylethanolamines can be exemplified by dimyristoyl phosphatidylethanolamine, dipalmitoyl phosphatidylethanolamine, distearoyl phosphatidylethanolamine, etc. Phosphatidyl inositols can be exemplified by phosphatidylinositol (sodium salt) derived from wheat, etc. Sphingomyelins can be exemplified by sphingomyelin derived from bovine brain etc. Phosphatidic acids and long-chain alkyl phosphates are exemplified by dimyristoyl phosphatidic acid, dipalmitoyl phosphatidic acid, distearoyl phosphatidic acid, dicetyl phosphate, etc. Gangliosides are exemplified by ganglioside GM1 and ganglioside GD1a, ganglioside GT1b, etc. Glycolipids are exemplified by galactosyl ceramide, glucosyl ceramide, lactosyl ceramide, phosphatide, globoside, etc. Phosphatidyl glycerols can be exemplified by dimyristoyl phosphatidylglycerol, dipalmitoyl phosphatidylglycerol, distearoyl phosphatidylglycerol, etc. The preferred lipid that constitutes the liposome is a combination of a phospholipid containing phosphorus and cholesterol. In particular, a combination of phosphatidylcholine that is a type of phospholipid and cholesterol is more preferred. Where a liposome is produced using a phospholipid and cholesterol, the molar ratio of the phospholipid to cholesterol is preferably in the range of 1:0 to 1:1.5 and more preferably in the range of 1:0.5 to 1:1.25.

The term "water-miscible organic solvent" as used herein refers to an organic solvent that can be misced with water, exemplified by alcohols, ethers, esters, ketones, and acetals. A preferred water-miscible organic solvent to be used is one or more organic solvents selected from 1-propanol, isopropyl alcohol, 2-butoxyethanol and t-butanol.

As for the concentration of the water-miscible organic solvent in the above-described aqueous solution, the optimal concentration must be selected, depending on the lipid composition and lipid concentration. This is because when increasing the concentration of the water-miscible organic solvent, the solubility of the lipid is increased, but as a result liposomes are not formed. Moreover, at the same time, since the water-miscible organic solvent easily remains with the liposomes, they can exert an unfavorable effect on the living body into which they have been introduced. Therefore, preferably, the concentration of the water-miscible organic solvent in the aqueous solution is the lowest possible to dissolve one or more lipids in the solution by mixing the solution with the lipids and heating the mixture. Specifically, the concentration of the water-miscible organic solvent is preferably 5 to 30% by volume, relative to the total volume of the aqueous solution, more preferably 5 to 20% by volume, and even more preferably 12 to 20% by volume. Where the water-miscible organic solvent is t-butanol, the concentration is particularly preferably 12 to 18% by volume, relative to the total volume of the aqueous solution. Where the water-miscible organic solvent is 1-propanol, the concentration is particularly preferably 5 to 19% by volume, relative to the total volume of the aqueous solution. Where the water-miscible organic solvent is 2-propanol, the concentration is particularly preferably 13 to 26% by volume, relative to the total volume of the aqueous solution. Where the water-miscible organic solvent is 2-butoxyethanol, the concentration is particularly preferably 6 to 9% by volume, relative to the total volume of the aqueous solution.

The mixture may be prepared by adding one or more lipids to an aqueous solution containing a water-miscible organic solvent in the above-mentioned concentration or may be prepared by dissolving one or more lipids in a water-miscible organic solvent and adding water thereto to give the above-mentioned concentration. In addition, the mixture may contain a sugar such as a disaccharide or polysaccharide as an osmotic adjusting agent. Preferred sugar is sucrose, a disaccharide. The concentration of sucrose is preferably 5 to 70 wt/vol %, more preferably 8 to 50 wt/vol %, of the amount of the aqueous solution containing water and a water-miscible organic solvent.

<Method of Producing Liposomes>

The method for producing liposomes according to the present invention may employ any known method or may omit any step, as long as the method includes the steps of heating a mixture of one or more lipids, water, and a water-miscible organic solvent to a temperature in a range of 62° C. to 80° C., maintaining the mixture after the heating step at a temperature of 40° C. or higher but lower than the temperature of the heating temperature for a predetermined period of time, and further cooling the mixture after the maintaining step. More specifically, in order to adjust the diameters of liposomes, the method of the present invention may be combined with, for example, an ultrasonic irradiation, extrusion, French press, or homogenization.

The heating temperature is not particularly limited as long as it is at or above the temperature at which the lipid is dissolved in the aqueous solution containing a water-miscible organic solvent and at which the aqueous solution does not become turbid. The heating temperature varies depending on the type of the lipid, the concentration of the lipid, the type of the water-miscible organic solvent, etc., but, in general, it is preferably in the range of 62 to 80° C., particularly preferably in the range of 65 to 72° C. It should be noted that where t-butanol serves as the water-miscible organic solvent and phosphatidylcholine as well as cholesterol serve as the lipids, the heating temperature is preferably in the range of 62 to 72° C.

The temperature in the maintaining step is not particularly limited as long as it is lower than the heating temperature and it allows formation of liposomes, and is preferably in a range of 40° C. to the heating temperature. The time for maintaining the temperature is preferably a time necessary to obtain a predetermined average diameter of liposomes. In the maintaining step, the mixture may be stepwise cooled at two or more different temperatures within the range of 40° C. to the heating temperature by maintaining at each temperature for a predetermined period of time.

The cooling temperature is not particularly limited as long as it is lower than the temperature in the maintaining step, and is preferably in a range of 0 to 40° C., more preferably in a range of 4° C. to 35° C., most preferably in a range of 20° C. to 30° C. The cooling step may be performed by natural cooling or using a cooling device.

In the method for producing liposomes according to the present invention, in order to render the particles in the liposome suspension more uniform in particle size, a known sizing means may be concurrently used. For example, liposomes with a desirable pore size may be obtained by passing the liposome suspension through a membrane with the specific pore size using gas pressure. Such a process of passing liposomes through a membrane with the specific pore size may be performed once or multiple times.

Embodiments of the liposome-producing apparatus 1 of the present invention will be described.

First Embodiment

Figure 2:
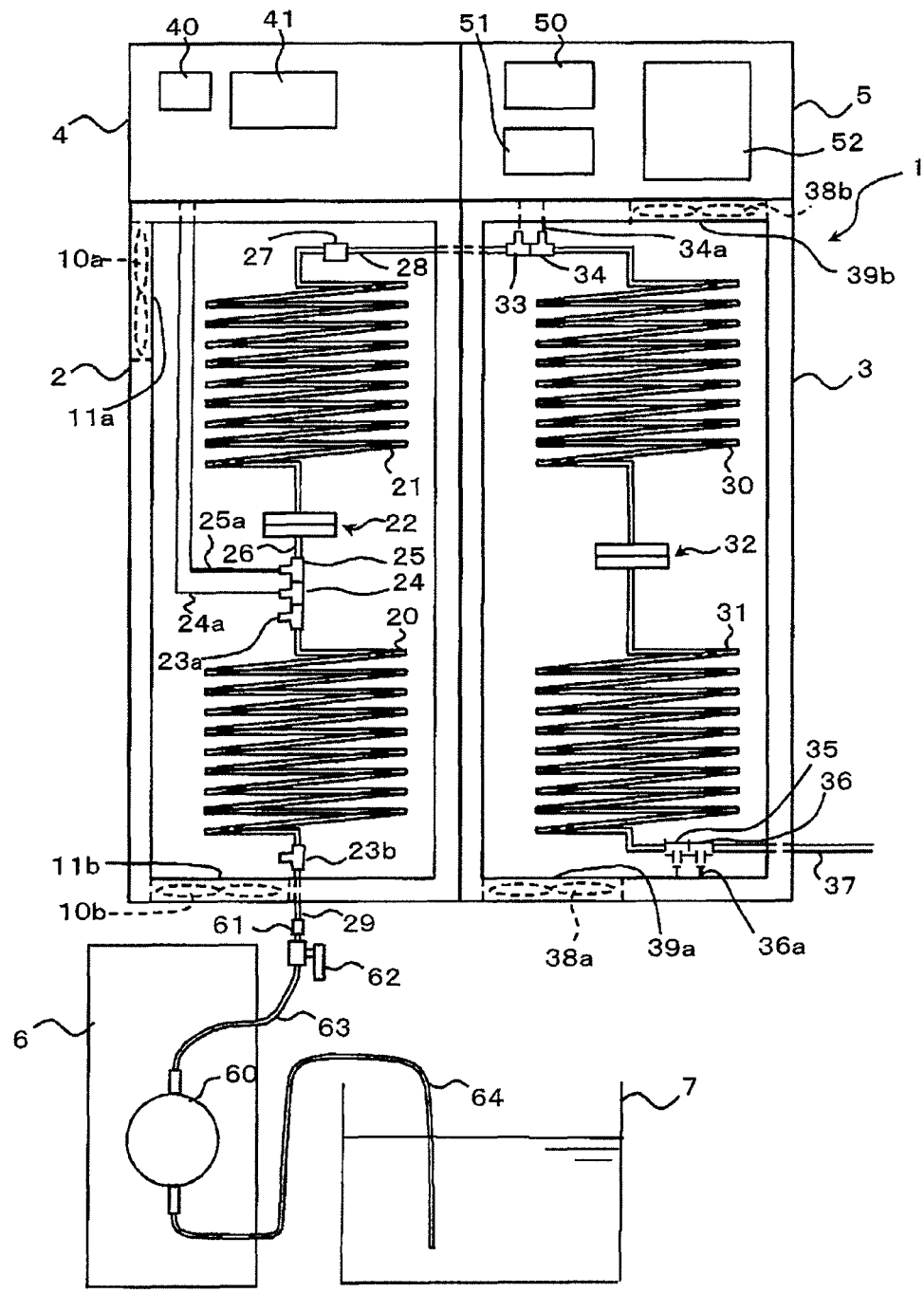
FIG. 2 is a schematic diagram illustrating the construction of a liposome-producing apparatus according to a first embodiment.

FIG. 2 is a schematic diagram illustrating the construction of a liposome-producing apparatus according to a first embodiment.

<1.1 Construction of Liposome-Producing Apparatus>

The liposome-producing apparatus 1 includes a dissolving zone and a first cooling zone. The dissolving zone includes a housing 2 for dissolution, having thermal insulation, and a solution sending channel, described below, being housed in the housing 2 for dissolution. The first cooling zone includes a first housing 3 for cooling, having thermal insulation, and a solution sending channel, described below, being housed in the first housing 3 for cooling. The housing 2 for dissolution is a casing member for heating a mixture that flows in the solution sensing channel and that is composed of one or more lipids and an aqueous solution containing a water-miscible organic solvent with a heat medium in the housing for dissolving the lipid or lipids in the aqueous solution. The first housing 3 for cooling is a casing member located on the downstream side of the housing 2 for dissolution in the solution sending direction for cooling the solution that is sent from the housing 2 for dissolution and flows in the solution sending channel with the heat medium in the housing 3 to a temperature that is lower than the temperature of the first housing 3 for cooling and that allows formation of liposomes.

The interior of the housing 2 for dissolution may be controlled at an approximately constant temperature, and thereby the temperature transition in the solution sending channel, described below, can be maintained constant. Specifically, as shown in FIG. 2, the wall surface of the housing 2 for dissolution is provided with a supply fan 10*a* for supplying air into the housing 2 for dissolution and an exhaust fan 10*b* for exhausting air from the housing 2 for dissolution. The supply fan 10*a* can send air having a controlled temperature into the housing through an opening 11*a* provided in the wall of the housing 2 for dissolution. The exhaust fan 10*b* can exhaust air from the housing through an opening 11*b* that is different from the opening 11*a*. Thus, the air in the housing 2 for dissolution is circulated to maintain the interior of the housing 2 at a constant temperature. More specifically, in the housing 2 for dissolution, the supply fan 10*a* is installed at the upper side, and the exhaust fan 10*b* is installed at the lower side. By doing so, warm air in the housing 2 for dissolution is prevented from stagnating upward by convection to maintain the entire interior of the housing 2 for dissolution at a constant temperature. Thus, the entire interior of the housing 2 for dissolution is maintained at a constant temperature, and thereby the entire solution sending channel in the housing 2 for dissolution is maintained at a temperature for dissolving the lipid and so on over the solution sending direction.

The housing 2 for dissolution is equipped with a tube 20, a tube 21, and a sterilization filter 22 disposed between the tubes 20 and 21. The tube 20, the sterilization filter 22, and the tube 21 are connected in series in this order in a direction for a mixture of the lipid or lipids and the aqueous solution to flow. The tubes 20 and 21 each have a coiled shape. The sterilization filter 22 is, for example, made of stainless steel provided with a filter therein and has a thin disk-like shape. The filter may be any filter having a pore size that can sterilize a fluid flowing in the tube. For example, a filter having a 0.2 micrometer pore size can be used. Between the tube 20 and the sterilization filter 22, T-shaped joints 23*a*, 24, and 25 and a tube 26 are connected in this order. The tube 20 is connected to a T-shaped joint 23*b* on the upstream side in the solution sending direction. Here, the channels at least in the tubes 20, 21, and 26 and the T-shaped joints 23*a*, 23*b*, 24, and 25 configure the solution sending channel of the housing 2 for dissolution. The total length of these channels for sending a solution is determined so as to be sufficient for at least dissolving a lipid or lipids in an aqueous solution. The solution sending channel may include a tube 28 and a part of a tube 29 inside the housing 2 for dissolution and/or the channel inside the sterilization filter 22. These channels for sending a solution are each sufficiently thin so that the temperature of a solution is maintained approximately uniform in a radial direction of the channel. The temperature of each thin channel is maintained constant over the longitudinal direction thereof. As a result, the temperature transition of a solution in the channels can be maintained constant by these thin channels.

The T-shaped joint 23*a* is used for connecting another tube in the route from the tube 20 to the tube 21, and the T-shaped joint 23*b* is used for connecting another tube in the route from the tube 29 to the tube 20. Their connecting part is closed when no other tube is connected thereto. The T-shaped joint 24 is used for connecting a pipe 24*a* that is connected to a pressure sensor (not shown, the same hereinafter) for measuring the pressure of an aqueous solution flowing from the tube 20 to the tube 21. The T-shaped joint 25 is used for connecting a temperature sensor (e.g., thermocouple) 25*a* for measuring the temperature of the aqueous solution.

The tube 21 is connected to a tube 28 through an I-shaped joint 27 on the downstream side in the solution sending direction. The tube 28 extends from the housing 2 for dissolution to the first housing 3 for cooling. The upstream side of the tube 20 in the solution sending direction is connected to a tube 29 extending from the T-shaped joint 23*b* to the outside of the housing 2 for dissolution.

The interior of the first housing 3 for cooling may be controlled at an approximately constant temperature, and thereby the temperature transition in the solution sending channel, described below, can be maintained constant. Specifically, as shown in FIG. 1, the wall surface of the first housing 3 for cooling is provided with a supply fan 38*a* for supplying air into the first housing 3 for cooling and an exhaust fan 38*b* for exhausting air from the first housing 3 for cooling. The supply fan 38*a* can send air having a controlled temperature into the housing through an opening 39*a* provided in the wall of the first housing 3 for cooling. The exhaust fan 38*b* can exhaust air from the housing through an opening 39*b* that is different from the opening 39*a*. Thus, air in the first housing 3 for cooling is circulated to maintain the interior of the first housing 3 for cooling at a constant temperature. More specifically, in the first housing 3 for cooling, the supply fan 38*a* is installed at the lower side, and the exhaust fan 38*b* is installed at the upper side. By doing so, cold air in the first housing 3 for cooling is prevented from stagnating downward by convection to maintain the entire interior of the first housing 3 for cooling at a constant temperature. Thus, the entire interior of the first housing 3 for cooling is maintained at a constant temperature, and thereby the entire solution sending channel in the first housing 3 for cooling is maintained at a temperature for forming liposomes over the solution sending direction.

The first housing 3 for cooling is equipped with a tube 30, a tube 31, and a sterilization filter 32 disposed between the tubes 30 and 31. The tube 30, the sterilization filter 32, and the tube 31 are connected in series in this order in the direction for the mixture that has passed through the housing 2 for dissolution to flow. The tubes 30 and 31 each have a coiled shape. The sterilization filter 32 is, for example, made of stainless steel provided with a filter therein and has a thin disk-like shape. The filter may be any filter having a pore size that can sterilize a fluid flowing in the tube. For example, a filter having a pore size larger than that of the sterilization filter 22, such as a filter of 1 micrometer diameter, can be used. Between the tube 28 extending from the housing 2 for dissolution and the tube 30 in the first housing 3 for cooling, T-shaped joints 33 and 34 are connected in this order. The tube 31 is connected to T-shaped joints 35 and 36 and a tube 37 in this order on the downstream side in the solution sending direction. The tube 37 extends to the outside from the first housing 3 for cooling. Here, the channels at least in the tubes 30 and 31 and the T-shaped joints 33, 34, 35, and 36 configure the solution sending channel of the first housing 3 for cooling. The total length of these channels for sending a solution in the first housing 3 for cooling is determined so as to be sufficient for at least maintaining the solution at a temperature allowing formation of liposomes for a predetermined period of time. The solution sending channel may include the tube 28 in the housing 2 for dissolution and apart of the tube 37 and/or the channel inside the sterilization filter 32. These channels for sending a solution are each sufficiently thin so that the temperature of a solution is maintained approximately uniform in a radial direction of the channel. The temperature of each thin channel is maintained constant over the length direction thereof. Since the solution sending channel of the housing 2 for dissolution and the solution sending channel of the first housing 3 for cooling are connected to each other, liposomes can be formed when the solution is continuously sent from the solution sending channel of the housing 2 for dissolution to the solution sending channel of the first housing 3 for cooling. By forming liposomes in such a way while continuously sending the solution, even if a temperature gradient occurs in the housing 2 for dissolution or the first housing 3 for cooling, the solution in the solution sending channel is hardly affected by the temperature gradient, and progress of the reaction at a constant temperature transition can be expected. In particular, the temperature transition of the solution supplied to the first housing 3 for cooling can be brought and maintained constant in a small amount of time by employing micro channels as the solution sending channels.

A T-shaped joint 33 is used for installing a turbidity sensor (not shown, the same hereinafter) for measuring the turbidity of a mixture flowing from the tube 28 to the tube 30. A T-shaped joint 34 is used for connecting a temperature sensor (e.g., thermocouple) 34a for measuring the temperature of the mixture. A T-shaped joint 35 is used for installing a turbidity sensor for measuring the turbidity of a mixture flowing from the tube 31 to the tube 37. A T-shaped joint 36 is used for connecting a temperature sensor (e.g., thermocouple) 36a for measuring the temperature of the mixture.

The liposome-producing apparatus 1 includes a controller 4 and a controller 5. The controller 4 can perform temperature setting, control the temperature inside the housing 2 for dissolution based on information of the temperature measured by the temperature sensor 25a, and measure the pressure of the mixture in the tube 26. Furthermore, the controller 4 preferably has a function of giving a warning when the pressure of a mixture flowing in the tube 26 is higher than a predetermined level. The temperature sensor 25a and the pressure sensor are both connected to the controller 4. The controller 4 includes an operation portion 40 for temperature setting and a display portion 41 for displaying the temperature measured by the temperature sensor 25a and the pressure measured by the pressure sensor.

The controller 5 can perform temperature setting, control the temperature inside the first housing 3 for cooling based on information of each temperature measured by the temperature sensor 34a and/or the temperature sensor 36a, and measure the turbidity of the mixture in the tubes 28 and 37. The temperature sensors 34a and 36a and the turbidity sensor are all connected to the controller 5. The controller 5 includes an operation/display portion 52 for temperature setting and displaying temperatures and turbidity displays 50 and 51 each displaying the turbidity measured by the turbidity sensors. The temperature inside the first housing 3 for cooling may be controlled by the temperature sensor 34a alone, the temperature sensor 36a alone, or both the temperature sensors 34a and 36a.

The temperature of the first housing 3 for cooling when a mixture of a lipid or lipids and an aqueous solution flows is set to a temperature lower than the temperature of the housing 2 for dissolution. The temperature of the housing 2 for dissolution is set to or above a temperature at which the lipid or lipids can be dissolved in the aqueous solution. On the other hand, the temperature of the first housing 3 for cooling is set to a temperature at which the lipid or lipids having been dissolved in the aqueous solution is cooled to form liposomes. Accordingly, the lipid or lipids in the mixture from the tube 29 are dissolved in the aqueous solution in the mixture when the mixture flows in the tube 20, the sterilization filter 22, and the tube 21. Subsequently, the mixture passes through the tube 28 and enters the first housing 3 for cooling. The mixture is cooled to form liposomes when it flows in the tube 30, the sterilization filter 32, and the tube 31.

The tubes 20, 21, 30, and 31 are each wound in a coiled shape, so that the temperature of the mixture flowing in each tube in the zones 2 and 3 is maintained for a predetermined period of time. In the case where the materials of the tubes 20, 21, 30, and 31 have good thermal conductivity, the case where the mixture supplied from the tube 29 is heated in advance, or the case where the difference in temperature between the housing 2 for dissolution and the first housing 3 for cooling is small, all the tubes 20, 21, 30, and 31 are not necessarily in a coiled shape. In this embodiment, for example, each tube constituting the solution sending channel has an inner diameter of 1/16 inch (approximately 1.6 mm). The inner diameter is not limited to this and may be larger or smaller than 1/16 inch. For example, in order to maintain a uniform temperature in a radial direction of the channel, the inner diameter is preferably set in a range of 1.0 to 3.0 mm. The inner diameter of the solution sending channel can be set to a size to easily generate a turbulent flow. In such a case, the solution in the solution sending channel is stirred, and thereby a reaction is performed under uniformly controlled temperature.

<1.2 Construction of Mixture Feeder>

A solution-sending pump 6 is located on the upstream side of the liposome-producing apparatus 1 in the solution sending direction, and a raw material container 7 is located on the upstream side of the solution-sending pump 6. The solution-sending pump 6 is equipped with a solution-sending portion 60 for sending a liquid from the raw material container 7 to the housing 2 for dissolution. The solution-sending portion 60 is connected to the housing 2 for dissolution via a tube 63, a valve 62, and an I-shaped joint 61 in this order. The solution-sending portion 60 is also connected to a tube 64 for feeding a mixture to the solution-sending pump 6 from the raw material container 7. The tubes 63 and 64 may be made of, for example, a material having flexibility, such as a resin, or may be made of a material such as a metal. The solution-sending pump 6 may be any pump. For example, a plunger pump, a syringe pump, or a roller pump can be used. The valve 62 may be any valve. For example, a manual rotary valve, an air valve, or an electromagnetic valve can be used.

<1.3 Supply of Mixture>

The raw materials for forming liposomes contained in the raw material container 7 at least include one or more lipids, water, and a water-miscible organic solvent. The mixture containing the one or more lipids, water, and the water-miscible organic solvent is suctioned from the raw material container 7 with the solution-sending pump 6 and is sent to the housing 2 for dissolution and then to the first housing 3 for cooling of the liposome-producing apparatus 1. In the case of mixing raw materials in the raw material container 7, the mixing is performed, for example, by manually shaking, stirring with a stirring bar or an agitating blade, or using an ultrasonic vibrator.

<1.4 Treatment in Liposome-Producing Apparatus>

The mixing step is performed by charging raw materials for forming liposomes, such as one or more lipids, water, and a water-miscible organic solvent, in the raw material container 7 and stirring them. The heating step is performed by allowing the mixture to pass through the housing 2 for dissolution being warmed to or above a temperature at which the lipid or lipids can be dissolved in the aqueous solution containing the water-miscible organic solvent. The temperature of the housing 2 for dissolution is preferably in the range of 62° C. to 80°

C., in particular, in the range of 65° C. to 72° C., as described above. The cooling step is performed by sending the mixture from the housing 2 for dissolution to the first housing 3 for cooling which is maintained at a temperature lower than the temperature of the housing 2 for dissolution. The temperature of the first housing 3 for cooling may be any temperature that is lower than the temperature of the housing 2 for dissolution and that allows formation of liposomes, and is preferably in a range of 40° C. to the heating temperature, as described above.

Second Embodiment

Figure 3:
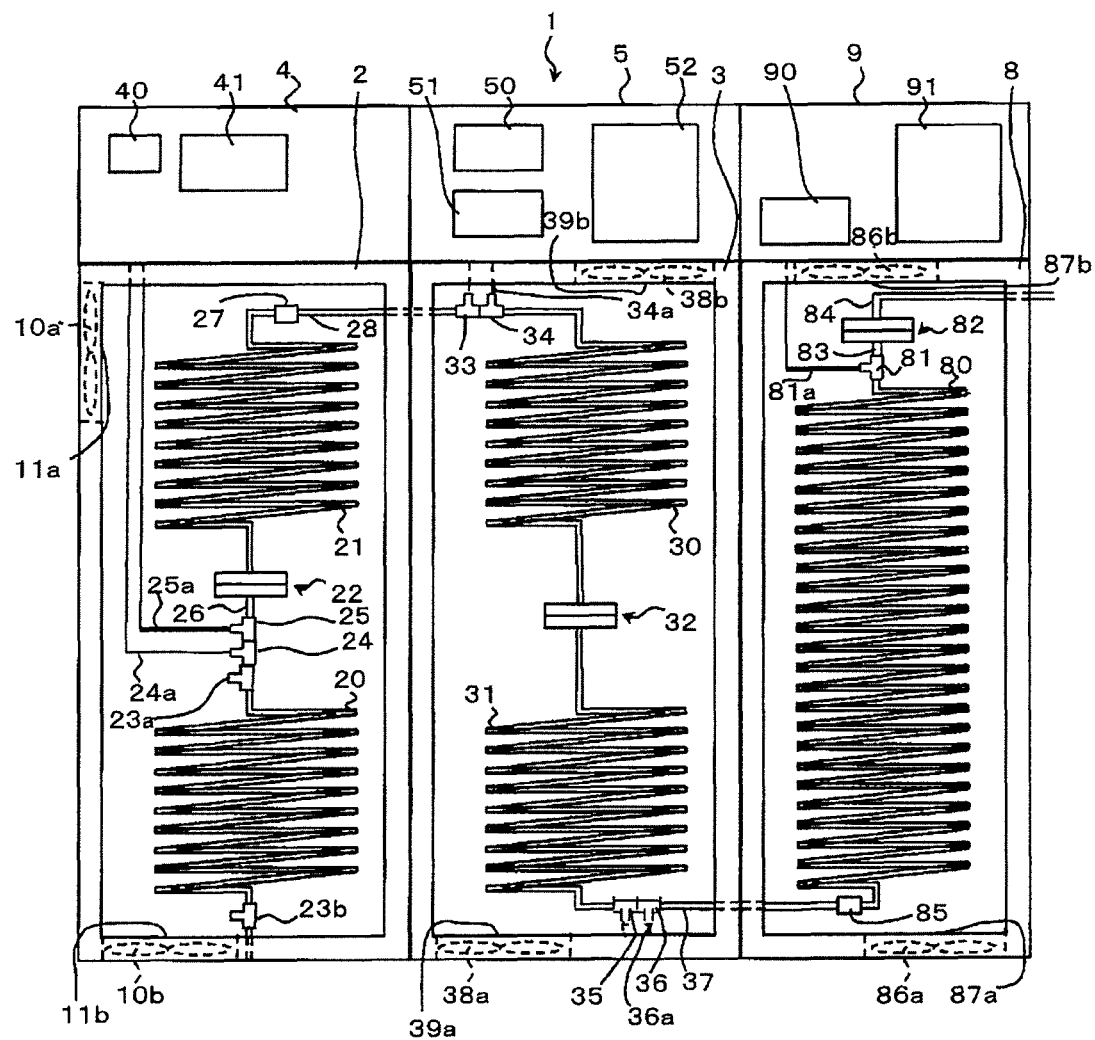
FIG. 3 is a schematic diagram illustrating the construction of a liposome-producing apparatus according to a second embodiment.

FIG. 3 is a schematic diagram illustrating the construction of a liposome-producing apparatus 1 according to a second embodiment.
<2.1 Construction of Liposome-Producing Apparatus>

The liposome-producing apparatus 1 includes a second cooling zone, in addition to the construction of the first embodiment. The second cooling zone includes a second housing 8 for cooling, having thermal insulation, and a solution sending channel, described below, housed in the second housing 8 for cooling. The second housing 8 for cooling is located on the downstream side of the first housing 3 for cooling in the solution sending direction. In the second housing 8 for cooling, the solution from the first housing 3 for cooling is cooled to a temperature lower than the temperature of the first housing 3 for cooling. The housing 2 for dissolution and the first housing 3 for cooling are the same as those in the liposome-producing apparatus 1 according to the first embodiment, and thus descriptions of the constructions thereof are omitted.

The interior of the second housing 8 for cooling may be controlled at an approximately constant temperature, and thereby the temperature transition in the solution sending channel can be made constant. Specifically, as shown in FIG. 3, the wall surface of the second housing 8 for cooling is provided with a supply fan 86*a* for supplying air into the second housing 8 for cooling and an exhaust fan 86*b* for exhausting air from the second housing 8 for cooling. The supply fan 86*a* can send air into the housing through an opening 87*a* provided in the wall of the second housing 8 for cooling. The exhaust fan 86*b* can exhaust air from the housing through an opening 87*b* that is different from the opening 87*a*. Thus, air in the second housing 8 for cooling is circulated to maintain the interior thereof at a constant temperature. More specifically, in the second housing 8 for cooling, the supply fan 86*a* is installed at the lower side, and the exhaust fan 86*b* is installed at the upper side. By doing so, cold air in the second housing 8 for cooling is prevented from stagnating downward by convection to maintain the entire interior of the second housing 8 for cooling at a constant temperature. Thus, the entire interior of the second housing 8 for cooling is maintained at a constant temperature, and thereby the entire solution sending channel in the second housing 8 for cooling is maintained at an approximately constant temperature over the solution sending direction.

The second housing 8 for cooling is equipped with a tube 80, a sterilization filter 82, etc. The tube 80 and the sterilization filter 82 are connected in series in this order in the direction for allowing the mixture passed through the first housing 3 for cooling to flow. The tube 80 has a coiled shape. The sterilization filter 82 is, for example, made of stainless steel provided with a filter therein and has a thin disk-like shape. The filter may be any filter having a pore size that can sterilize a fluid flowing in the tube. For example, a filter having a pore size of 1 micrometer can be used. The tube 37 extending from the first housing 3 for cooling is connected to one end of the tube 80 on the upstream side in the solution sending direction with a T-shaped joint 85. Between one end of the tube 80 on the downstream side in the solution sending direction and the sterilization filter 82, a T-shaped joint 81 and a tube 83 are connected in this order. The T-shaped joint 81 is used for connecting a temperature sensor (e.g., thermocouple) 81*a* for measuring the temperature of the mixture passing through the tubes 80 and 83. The sterilization filter 82 is connected to a tube 84 on the downstream side in solution sending direction. The tube 84 extends to the outside from the second housing 8 for cooling.

The liposome-producing apparatus 1 includes a controller 4, a controller 5, and a controller 9. The controller 4 and the controller 5 are the same as those of the liposome-producing apparatus 1 according to the first embodiment, and thus descriptions of their constructions are therefore omitted.

The controller 9 can perform temperature setting, and control the temperature inside the second housing 8 for cooling based on information of the temperature measured by the temperature sensor 81*a*. The temperature sensor 81*a* is connected to the controller 9. The controller 9 includes an operation portion 90 for temperature setting and a display portion 91 for displaying the temperature measured by the temperature sensor 81*a*.

The temperature of the second housing 8 for cooling is set to be lower than the temperature of the first housing 3 for cooling. The mixture containing liposomes passed through the first housing 3 for cooling is cooled at a predetermined cooling rate. The temperature of the second housing 8 for cooling is not particularly limited as long as it is in a temperature range lower than the temperature of the first housing 3 for cooling, preferably in a temperature range of 0° C. to 40° C., in particular, in a temperature range of 20° C. to 30° C., as described above. By providing the second housing 8 for cooling, rapid cooling of liposomes can be effectively performed. Accordingly, for example, an encapsulation material that should not be heated too much can be encapsulated in the liposomes to prevent deterioration.

The tube 80 is wound in a coiled shape, so that the temperature of the mixture flowing in the tube 80 in the second housing 8 for cooling is maintained for a predetermined period of time. In the case where the material of the tube 80 has good thermal conductivity, the tube 80 is not necessarily in a coiled shape. In this embodiment, the diameter of the tube as a path for a mixture is 1/16 inch. The inner diameter is not limited to this and may be larger or smaller than 1/16 inch.

The tube 29 on the upstream side in the solution sending direction of the liposome-producing apparatus 1 can be connected to devices similar to the solution-sending pump 6 and the raw material container 7 in the liposome-producing apparatus 1 according to the first embodiment.

Third Embodiment

Figure 4:
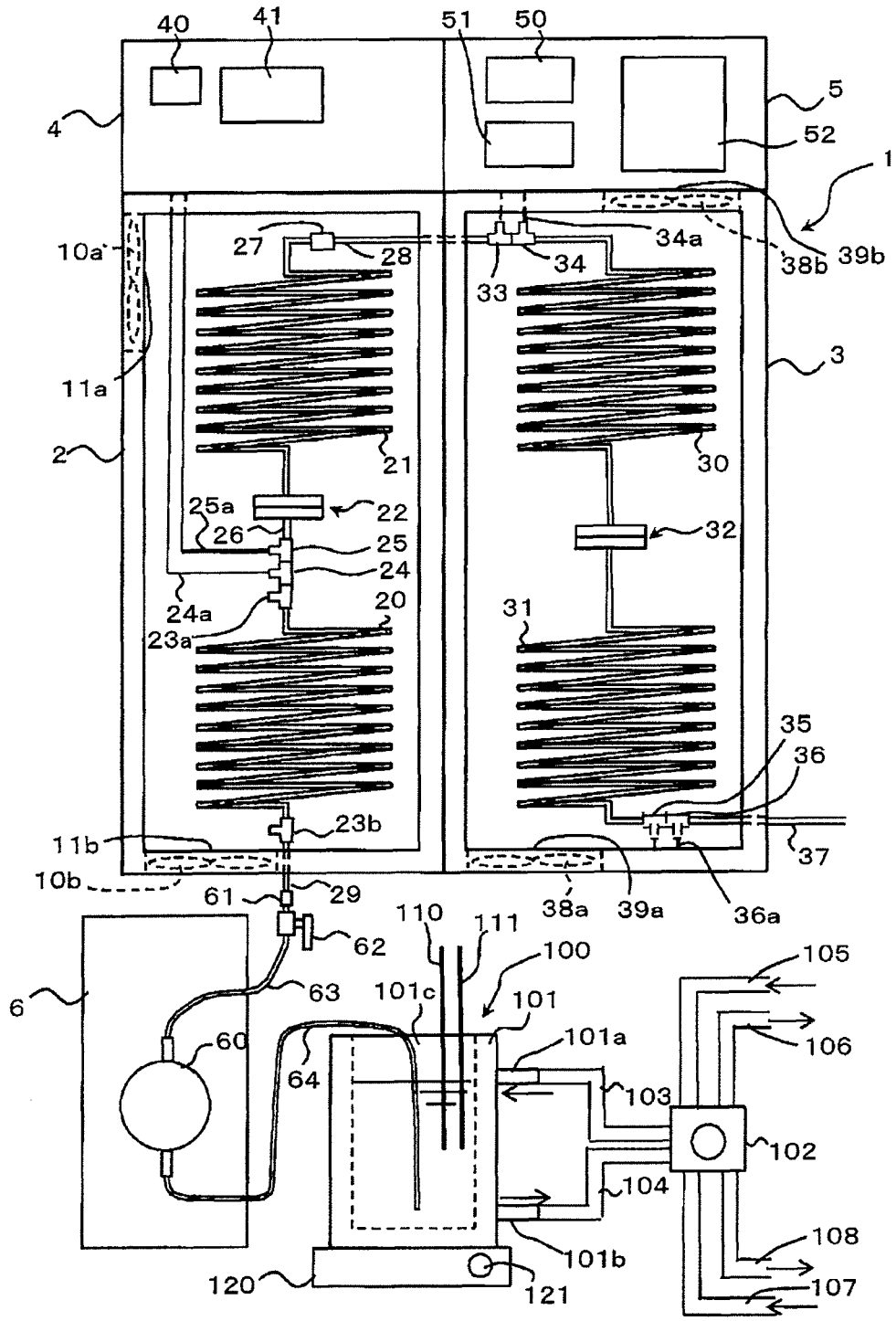
FIG. 4 is a schematic diagram illustrating the construction of a liposome-producing apparatus according to a third embodiment.

FIG. 4 is a schematic diagram illustrating the construction of a liposome-producing apparatus according to a third embodiment.
<3.1 Construction of Liposome-Producing Apparatus>

The liposome-producing apparatus 1 includes a preliposome-forming device 100, in addition to the construction of the first embodiment. The housing 2 for dissolution and the first housing 3 for cooling are the same as those in the liposome-producing apparatus 1 according to the first embodiment, and thus descriptions of the constructions thereof are omitted. The preliposome-forming device 100 is located on the upstream side of the housing 2 for dissolution in the solution sending direction. The solution-sending pump 6 described in the first embodiment is located between the housing 2 for dissolution and the preliposome-forming device 100. The constructions of the solution-sending pump 6 and the connection of the solution-sending pump 6 to the housing 2 for dissolution are the same as those in the first embodiment and have been already described. Descriptions thereof are therefore omitted here.

The preliposome-forming device 100 is a device for forming liposomes by heating a mixture containing one or more lipids, water, and a water-miscible organic solvent to dissolve the lipid or lipids in the aqueous solution and then decreasing the temperature to be lower than the dissolving temperature. The preliposome-forming device 100 includes a container 101, a switch valve 102, and a stirrer 120. Instead of the stirrer 120, for example, an agitator having a rotary shaft provided with a blade may be used. The container 101 has a space inside the peripheral wall and has two pipes 101a and 101b that connect the space to the outside. In addition, a space 101c surrounded by the peripheral wall is provided inside the container 101. The one or more lipids, water, and the water-miscible organic solvent as raw materials for liposomes are charged in this space 101c. The temperature and turbidity of the mixture containing the one or more lipids, water, and the water-miscible organic solvent charged in the space 101c are monitored by a temperature sensor 110 and a turbidity sensor 111.

The switch valve 102 has six connections in total. Two of these six connections are connected to the pipes 101a and 101b of the container 101 via tubes 103 and 104, respectively. The remaining four connections are connected to tubes 105, 106, 107, and 108, respectively. The tube 105 is used for supplying hot water; the tube 106 is used for exhausting hot water; the tube 107 is used for supplying cold water; and the tube 108 is used for exhausting cold water. The switch valve 102 can switch from the pattern A for connecting between the tube 105 and the tube 103 and between the tube 106 and the tube 104 to the pattern B for connecting between the tube 107 and the tube 103 and between the tube 108 and the tube 104. When the switch valve 102 is set to pattern A, hot water circulates inside the peripheral wall of the container 101. When the switch valve 102 is set to pattern B, cold water circulates inside the peripheral wall of the container 101. The stirrer 120 has a dial 121 that can change the rotation speed for stirring.

<3.2 Treatment in Preliposome-Forming Device>

Raw materials for forming liposomes, such as one or more lipids, water and a water-miscible organic solvent together with a stirring bar are charged in the container 101. The stirrer 120 is set to a predetermined rotation speed using the dial 121. Subsequently, the switch valve 102 is set to pattern A to circulate hot water inside the peripheral wall of the container 101. The temperature of the hot water is preferably in a range of 62° C. to 80° C., in particular, in a range of 65° C. to 72° C. By doing so, the lipid or lipids are dissolved in the aqueous solution. Subsequently, the switch valve 102 is set to pattern B to circulate cold water inside the peripheral wall of the container 101. The temperature of the cold water is preferably lower than 62° C., in particular, in a range of 20° C. to 30° C. As a result, the lipid or lipids in the container 101 are deposited out of the aqueous solution to form liposomes.

Subsequently, the housing 2 for dissolution is maintained at or above a temperature at which the lipid or lipids can be dissolved in an aqueous solution containing the water-miscible solvent. The first housing 3 for cooling is maintained at a temperature lower than the temperature of the housing 2 for dissolution. Then, the mixture containing the liposomes in the container 101 is sent to the housing 2 for dissolution by driving the solution-sending pump 6 and opening the valve 62. In the housing 2 for dissolution, the lipid or lipids forming the liposomes are dissolved in the aqueous solution. The mixture in the dissolved state is sent to the first housing 3 for cooling, and the lipid or lipids are deposited out of the aqueous solution to form liposomes. Thus, a suspension of one or more lipids uniformly mixed with an aqueous solution containing a water-miscible organic solvent can be easily obtained by using the preliposome-forming device 100. As a result, liposomes can be easily formed again in the subsequent dissolving zone and first cooling zone. That is, lipids are uniformly dissolved in an aqueous solution by using this preliposome-forming device 100, and thereby liposomes having uniform diameters tend to be easily produced in the subsequent dissolving zone and first cooling zone.

<3.3 Other Modifications>

The second housing 8 for cooling and the controller 9 thereof described in the second embodiment can be added to the construction of the third embodiment. In such a case, the mixture containing liposomes formed in the first housing 3 for cooling is cooled in the second housing 8 for cooling at a predetermined cooling rate.

Fourth Embodiment

Figure 5:
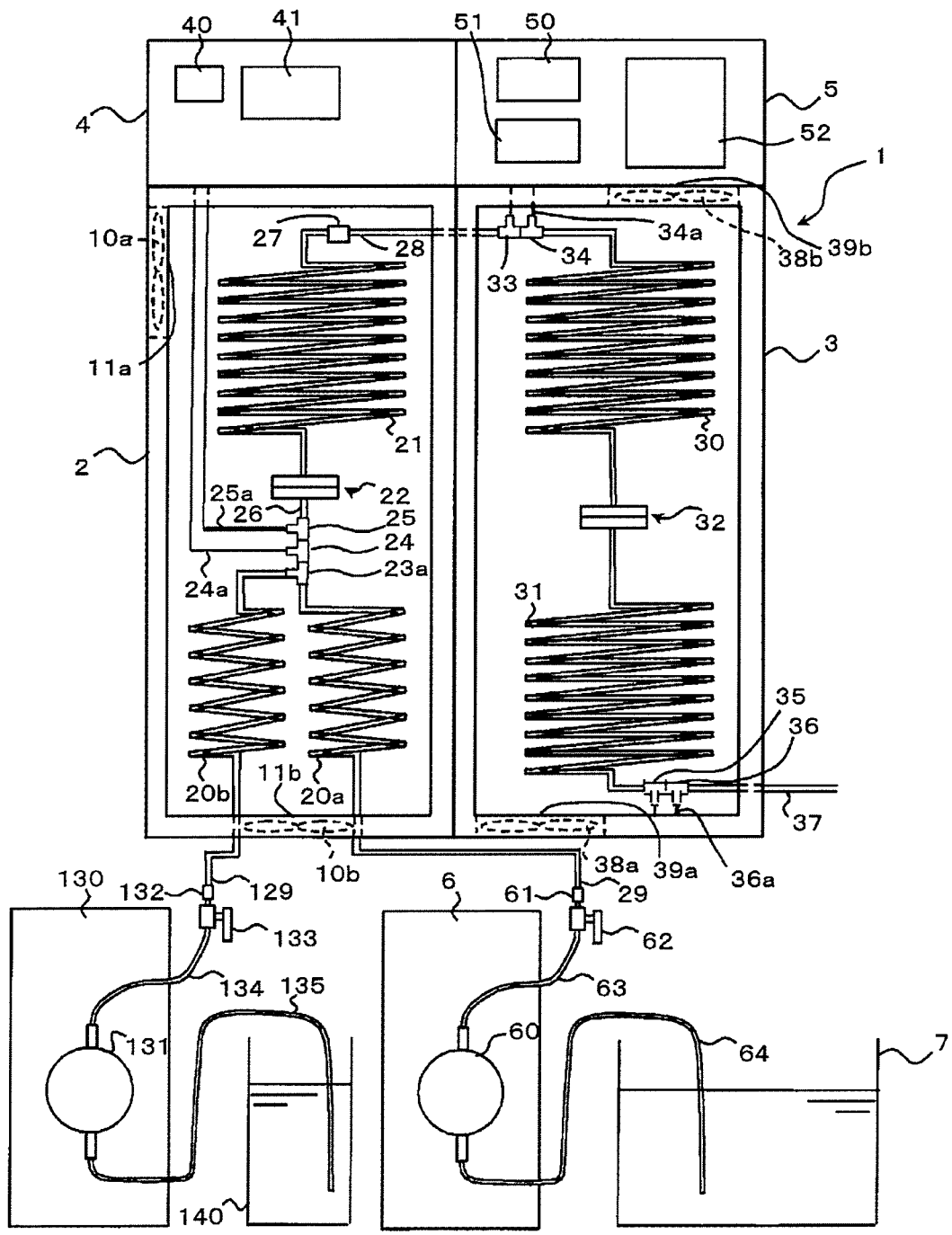
FIG. 5 is a schematic diagram illustrating the construction of a liposome-producing apparatus according to a fourth embodiment.

FIG. 5 is a schematic diagram illustrating the construction of a liposome-producing apparatus according to a fourth embodiment.

<4.1 Construction of Liposome-Producing Apparatus>

The liposome-producing apparatus 1 includes a housing 2 for dissolution and a first housing 3 for cooling similarly to the first embodiment. The first housing 3 for cooling is the same as the first housing 3 for cooling described in the first embodiment, and thus descriptions of the construction thereof are omitted. On the other hand, though the main construction of the housing 2 for dissolution is the same as that of the housing 2 for dissolution described in the first embodiment, the housing 2 for dissolution of the liposome-producing apparatus 1 according to the fourth embodiment is different from the housing 2 for dissolution of the liposome-producing apparatus 1 according to the first embodiment in terms of the construction on the upstream side than the T-shaped joint 23a in the solution sending direction. In the housing 2 for dissolution of the liposome-producing apparatus 1 according to the fourth embodiment, two coiled tubes 20a and 20b are branched from the T-shaped joint 23a on the upstream side of the T-shaped joint 23a in the solution sending direction. The end of the tube 20a on the upstream side in the solution sending direction is connected to a tube 29, and the tube 29 extends to the outside from the housing 2 for dissolution. The upstream side of the tube 29 is connected to a solution-sending pump 6 and further a raw material container 7 similarly to the liposome-producing apparatus 1 according to the first embodiment. The construction of the upstream side than the tube 29 in the solution sending direction is the same as that described in the first embodiment, and descriptions thereof are therefore omitted here.

The end of the tube 20b on the upstream side in the solution sending direction is connected to a tube 129, and the tube 129 extends to the outside from the housing 2 for dissolution. On the upstream side of the tube 129 in the solution sending direction, a solution-sending pump 130 and an encapsulation material container 140 serving as an encapsulation material feeder are disposed. The encapsulation material container 140 contains a liquid including a material to be encapsulated in liposomes (e.g., a pharmaceutical agent or a cosmetic material). The solution-sending pump 130 includes a solution-sending portion 131 for sending the liquid including the encapsulation material from the encapsulation material container 140 to the housing 2 for dissolution. Between the tube 129 and the solution-sending portion 131, an I-shaped joint 132, a valve 133, and a tube 134 are disposed in this order from the tube 129 side toward the upstream in the solution sending direction. The solution-sending portion 131 is also connected to a tube 135 for supplying a liquid to the solution-sending pump 130 from the encapsulation material container 140. The tubes 134 and 135 may be made of, for example, a material having flexibility, such as a resin, or may be made of a material such as a metal. The solution-sending pump 130 may be any pump, as in the solution-sending pump 6. For example, a plunger pump, a syringe pump, or a roller pump can be used. The valve 133 may be any valve, as in the valve 62. For example, a manual rotary valve, an air valve, or an electromagnetic valve can be used.

<4.2 Treatment in Preliposome-Forming Device>

Raw materials for forming liposomes, such as one or more lipids, water, a water-miscible organic solvent, are charged in the raw material container 7 and are stirred. An encapsulation material and a solvent therefor are charged in the encapsulation material container 140 and are stirred. In the case where the raw material container 7 or the encapsulation material container 140 contains a liquid mixed in advance, the stirring in the container 7 or 140 is not necessarily required. Subsequently, the housing 2 for dissolution is maintained at or above a temperature at which the lipid or lipids can be dissolved in an aqueous solution containing the water-miscible solvent. The first housing 3 for cooling is maintained at a temperature lower than the temperature of the housing 2 for dissolution. Then, the mixture containing the one or more lipids, water, and the water-miscible organic solvent in the raw material container 7 and the liquid in the encapsulation material container 140 are sent to the housing 2 for dissolution by driving the solution-sending pumps 6 and 130 and opening the valves 62 and 133. In the housing 2 for dissolution, the lipid or lipids forming liposomes are dissolved in the aqueous solution, and the aqueous solution is mixed with the liquid containing the encapsulation material from one side of the T-shaped joint 23a. The mixture of the liquid containing the encapsulation material and the solution dissolving the lipid or lipids is sent from the housing 2 for dissolution to the first housing 3 for cooling. In the first housing 3 for cooling, liposomes are formed by cooling, and the encapsulation material is incorporated into the liposomes. Subsequently, the solution containing liposomes encapsulating the encapsulation material therein is taken out from a tube 37 connected to the first housing 3 for cooling.

<4.3 Other Modifications>

Instead of the T-shaped joint 23a or on the upstream side or the downstream side of the T-shaped joint 23a, a mixer for mixing the fluids passed through the tube 20a and the tube 20b may be disposed. The second housing 8 for cooling and the controller 9 described in the second embodiment can be added to the construction of the fourth embodiment. In such a case, the mixture containing liposomes formed in the first housing 3 for cooling is cooled in the second housing 8 for cooling at a predetermined cooling rate. Alternatively, the preliposome-forming device 100 described in the third embodiment can be disposed instead of the raw material container 7 used in the liposome-producing apparatus 1 according to the fourth embodiment. Furthermore, both the second housing 8 for cooling and the preliposome-forming device 100 may be employed in the liposome-producing apparatus 1 according to the fourth embodiment.

Fifth Embodiment

Figure 6:
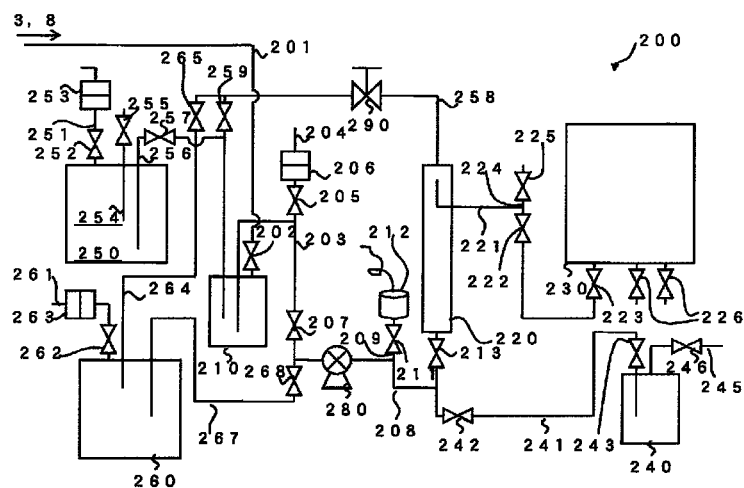
FIG. 6 is a schematic diagram illustrating an ultrafiltration device that is an optional component of a liposome-producing apparatus according to a fifth embodiment.
Figure 7:
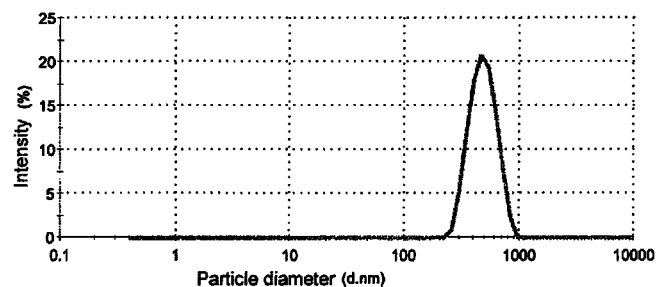
FIG. 7 is a particle size distribution chart of the liposome suspension prepared under the conditions of a t-butanol (t-BuOH) concentration of 16 vol % in Experimental Example according to the present invention.
Figure 8:
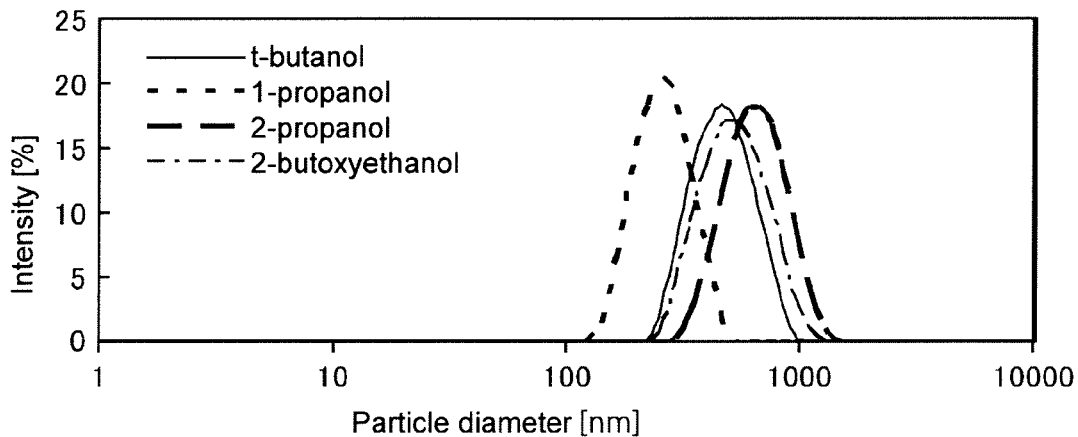
FIG. 8 shows the result of the particle size distribution obtained when liposome suspensions were prepared from aqueous solutions containing each water-miscible organic solvent using dipalmitoylphosphatidylcholine (DPPC), cholesterol, and stearylamine in an Example according to the present invention.
Figure 9:
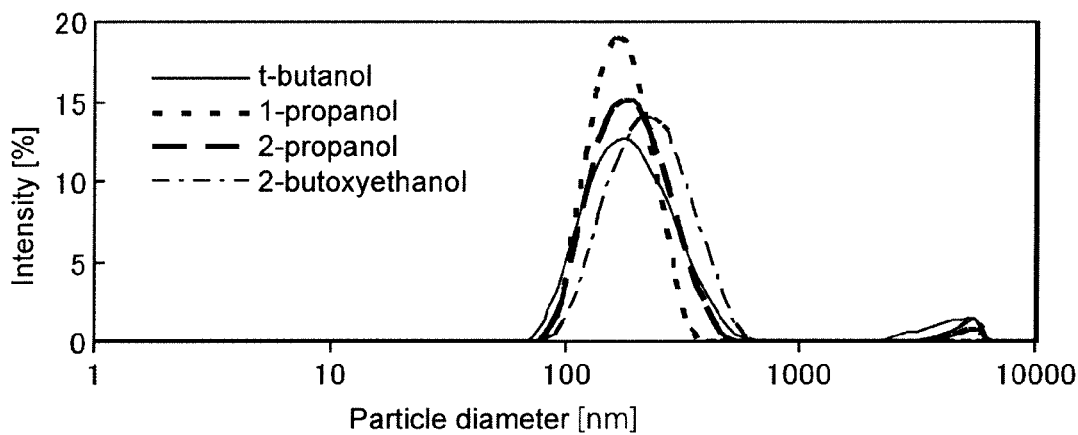
FIG. 9 shows the result of the particle size distribution obtained when liposome suspensions were prepared from aqueous solutions containing each water-miscible organic solvent using DPPC, cholesterol, and dipalmitoyl phosphatidylglycerol (DPPG) in an Example according to the present invention.

FIG. 6 is a schematic diagram illustrating an ultrafiltration device that is an optional component of a liposome-producing apparatus according to a fifth embodiment.

The liposome-producing apparatus 1 according to any one of the first to fourth embodiments can be connected to the ultrafiltration device (hereinafter, referred to as "UF device") 200 for filtrating the solution containing liposomes on the downstream side of the first housing 3 for cooling or the second housing 8 for cooling.

<5.1 Construction of UF Device>

UF device 200 includes a reservoir 210, a membrane module 220 as an example of a filtration means, a filtrate-collecting bag 230, a liposome-collecting bag 240, a liquid-exchanging buffer bag 250, a module-washing water bag 260, a circulating pump 280, and a pressure-regulating valve 290. The liquid-exchanging buffer bag 250 and the module-washing water bag 260 may not be necessarily provided. The reservoir 210 is a container for receiving a solution containing liposomes from the liposome-producing apparatus 1. The membrane module 220 removes the water-miscible organic solvent from the solution containing liposomes to concentrate the solution. In the case of forming liposomes encapsulating a material therein, the membrane module 220 removes the water-miscible organic solvent and the material being not encapsulated in the liposomes. The filtrate-collecting bag 230 is a bag for receiving a filtrate passed through the membrane module 220. The liposome-collecting bag 240 is a bag for collecting a liposome suspension after filtration with the membrane module 220. The liquid-exchanging buffer bag 250 is a bag for supplementing a liquid for the liquid flowing out by the filtration with the membrane module 220. The module-washing water bag 260 is a bag for containing a liquid for washing the membrane module 220. The circulating pump 280 is a pump for circulating a liquid flowing in each path of the UF device 200 and may be disposed at any position where the solution containing liposomes can be pumped to the membrane module 220. The pressure-regulating valve 290 is a valve for adjusting the pressure in the membrane module 220. The pressure-regulating valve 290 and the valves described below may be driven by any driving system, such as manually, electrically, or air-driven valves.

In the case where the first housing 3 for cooling or the second housing 8 for cooling of the liposome-producing apparatus 1 is provided, a tube 201 for supplying a solution containing liposomes from the second housing 8 for cooling side is connected to the upstream of the reservoir 210. A valve 202 is disposed between the tube 201 and the reservoir 210. A tube 203 connects between the reservoir 210 and the circulating pump 280, and a tube 204 is branched from the tube 203. The tube 204 is provided with a valve 205 and an air filter 206 in this order from the branching point side. The tube 203 is equipped with a valve 207 at a position between the branching point and the circulating pump 280.

The circulating pump 280 and the membrane module 220 are connected with a tube 208, and a tube 209 is branched from the tube 208. The tube 209 is equipped with a valve 211 and a pressure sensor 212 in this order from the branching point side. The tube 208 is equipped with a valve 213 at a position between the branching point and the membrane module 220.

The outlet of the membrane module 220 and the filtrate-collecting bag 230 are connected with a tube 221, and a tube 224 is branched from the tube 221. The tube 224 is equipped with a valve 225. The tube 221 is equipped with a valve 222 and a valve 223 in this order between the branching point and the filtrate-collecting bag 230. The filtrate-collecting bag 230 is equipped with two other tubes, and these tubes are connected to the respective valves 226.

The branching point of the tube 208 and the tube 209 and the valve 213 are connected with another tube 241. The tube 241 is equipped with a valve 242 and a valve 243 in this order from the branching point of the tube 241 and the tube 208. The liposome-collecting bag 240 is connected to a tube 245, and the tube 245 is equipped with a valve 246.

The liquid-exchanging buffer bag 250 is connected to a tube 251. The tube 251 is equipped with a valve 252 and an air filter 253 in this order from the connection with the liquid-exchanging buffer bag 250 side. The liquid-exchanging buffer bag 250 is equipped with a tube 254 extending toward the outside from the inside. The tube 254 is equipped with a valve 255 at the outside of the liquid-exchanging buffer bag 250. A tube 256 is disposed so as to extend from the inside of the liquid-exchanging buffer bag 250 to the inside of the reservoir 210. The tube 256 is equipped with a valve 257 outside both the liquid-exchanging buffer bag 250 and the reservoir 210.

Between the valve 257 and the outside of the reservoir 210, the tube 256 is connected to a tube 258 communicating with the outlet of the membrane module 220. The tube 258 is equipped with a pressure-regulating valve 290 and a valve 259 between the outlet of the membrane module 220 and the connection with the tube 256.

The module-washing water bag 260 is connected to a tube 261. The tube 261 is equipped with a valve 262 and a filter 263 in this order from the side of the connection of the module-washing water bag 260 with the tube 261. Between the pressure-regulating valve 290 and the valve 259, a tube 264 extends to the module-washing water bag 260. The tube 264 is provided with a valve 265. The inner bottom of the module-washing water bag 260 is connected to a tube 267 that extends between the valve 207 of the tube 203 and the circulating pump 280. The tube 267 is equipped with a valve 268.

<5.2 Various Examples of Operation of UF Device>
(1) Sterilization of UF Device

The components constituting the UF device 200, i.e., the membrane module 220, the reservoir 210, bags 230, 240, 250, and 260, and the wetted parts such as tubes connecting these components in a completely assembled state, are subjected to autoclave sterilization with an autoclave (not shown), for example, at 121° C. for 20 min. Alternatively, without using the autoclave, a sterile connection device may be disposed between the tube 37 on the outlet side of the first housing 3 for cooling or the tube 84 on the outlet side of the second housing 8 for cooling and the tube 201 on the inlet side of the UF device 200 for connecting the tube 37 (or 84) and the tube 201 under sterile conditions.

(2) Washing Treatment of Membrane Module

The membrane module 220 is washed with a water for injection before use. For example, washing water is sent to the membrane module 220 from the module-washing water bag 260 containing 5 L of pure water. Each valve is operated so that the washing water circulates (for example, valves 268, 213, 265, 222, and 223 are opened, and valves 207, 211, 242, 259, and 225 are closed), and the pure water is circulated by operating the circulating pump 280. The washing water is gradually filtrated by continuing the circulation and is collected in the filtrate-collecting bag 230. After accumulation of about 1 L of this filtrate, the circulation is stopped.

(3) Operation for Confirming Safety of Membrane Module

In order to confirm safety of the membrane module 220, an integrity test is carried out. The circulating fluid in the channel including the membrane module 220 and the circulating pump 280 is discharged, and the channel is closed by operating the pressure-regulating valve 290 on the downstream side of the membrane module 220. A pressure of about 5 psi is applied to the membrane module 220 by sending air with the circulating pump 280, and then the circulating pump 280 is stopped. The reduction of pressure in a 5 min period following the stop of the pump is recorded. When the pressure reducing rate is 0.5 psi/min or less, the membrane module is determined to have passed the integrity test. As this operation for confirming safety needs air from outside, the air is taken in through the air filter 206.

(4) Removal of Water-Miscible Organic Solvent (Concentration Treatment)

About 400 mL of a solution containing liposomes collected in the reservoir 210 is circulated at a flow rate of 700 mL/min with the circulating pump 280, and a pressure applied to the membrane module 220 is adjusted to about 10 psi by operating the pressure-regulating valve 290. The filtrate flowing out of the membrane module 220 is collected in the filtrate-collecting bag 230. A liquid in the same amount as the filtrate flowed out during this filtration operation is preferably supplemented from the liquid-exchanging buffer bag 250. The liquid circulation is continued, and the buffer exchange is terminated after collection of 4 L of the filtrate. The resulting liposome suspension from which the water-miscible organic solvent has been removed is collected in the liposome-collecting bag 240. In the case of forming liposomes encapsulating a material, the liposome suspension from which the water-miscible organic solvent and the material being not encapsulated in the liposomes have been removed is collected in the liposome-collecting bag 240. As this concentration treatment needs air from outside, the air is taken into the system through the air filter 253. The amount of the water-miscible organic solvent remaining in the liposome suspension is quantitatively measured by gas chromatography. The concentration of the water-miscible organic solvent remaining in the liposome suspension after the step of removing the water-miscible organic solvent under the above-described conditions was 756 ppm. Furthermore, after the completion of the operation, the integrity test of the membrane module 220 is carried out again to confirm the integrity of the membrane module 220 during the operation.

Embodiments of the present invention have been described above, but the present invention is not limited to these embodiments, and various modifications can be employed.

For example, the dissolving zone, the first cooling zone, and the second cooling zone may be formed within a single housing which is simply divided into the respective zones, instead of separately providing each of the housing 2 for dissolution, the first housing 3 for cooling, and the second housing 8 for cooling. The housing 2 for dissolution, the first housing 3 for cooling, and/or the second housing 8 for cooling may be realized by a bath containing a liquid such as warm water or cold water, wherein the liquid may be circulated in the housing 2 for dissolution, the first housing 3 for cooling, and/or the second housing 8 for cooling.

The tubes may be made of, for example, a metal, such as stainless steel, hastelloy, or Inconel, a resin, or glass. In case of formation of liposomes for pharmaceutical applications, glass can be used. In the embodiments described above, embodiments using a sterilization filter that is suitable for formation of liposomes for pharmaceutical applications have been described. If sterilization is unnecessary, the sterilization filter may not be used, or a filter not having a sterilizing effect may be used instead of the sterilization filter.

Examples

The Examples of the present invention will be described hereinbelow; however, the Examples should not be construed as limiting the present invention.

1. Materials for Liposomes a) Phospholipid

L-α-dipalmitoylphosphatidylcholine (DPPC) manufactured by Nippon Oil & Fats Co., Ltd. was used.

b) Cholesterol

Cholesterol (Chol.) manufactured by Sigma Chemical Co. was used.

c) Stabilizing Agent

Sucrose manufactured by Wako Pure Chemical Industries, Ltd. was used.

d) Water-Miscible Organic Solvents t-Butanol (t-BuOH; special grade) manufactured by Wako Pure Chemical Industries, Ltd., 1-propanol (special grade) manufactured by Wako Pure Chemical Industries, Ltd., 2-propanol (special grade) manufactured by Wako Pure Chemical Industries, Ltd., and 2-butoxyethanol (special grade) manufactured by Wako Pure Chemical Industries, Ltd. were used.

e) Lipids Other than a) and b)

Dipalmitoyl phosphatidylglycerol (DPPG), dipalmitoyl phosphatidylethanolamine (DPPE), and hydrogenated soy phosphatidylcholine (HSPC) were purchased from Nippon Oil & Fats Co., Ltd. Stearylamine (SA) and dicetyl phosphate (DCP) were purchased from a Wako Pure Chemical Industries, Ltd. and Sigma Chemical Corporation, respectively.

2. Method for Measuring Particle Size Distribution of Liposomes

Measurement of particle size distribution of the liposomes was performed using a particle size distribution measurement device (Zetasizer Nano ZS, manufactured by Malvern Instruments Ltd.) measured by dynamic light scattering. The liposomes prepared in the Example Experiment described later were subjected to size measurement after being diluted with phosphate buffered saline (PBS). The dilution was approximately 5000- to 10000-fold. The values measured with the Zetasizer Nano ZS were presented as the mean particle diameter, Z-Average (d. nm). Using the polydispersity index (PDI) values presented concurrently as the index, the uniformity of the liposome particle size distribution was evaluated.

Further, the results of the measurement displayed as "Result quality" on the above-mentioned particle size distribution measurement device were taken as the criteria for judging whether liposomes uniform in particle size had been formed. That is, when the liposomes met the quality standard defined by Malvern in particle diameter measurement, "Good" was displayed for "Result quality." When a "Good" was not displayed as a measurement result, it was judged that the samples were not uniform in particle size, unsuitable for dynamic light scattering.

3. Experiment Example

3.1: Examination of Temperature Ranges for Dissolving Phospholipid and Cholesterol 380 mg of DPPC and 200 mg of cholesterol were weighed in a glass vial, to which was added a mixture of 20 mL of 10 wt/vol % sucrose solution and 4.25 mL of t-BuOH. This vial was stirred for 10 min in a water bath maintained at 80° C. The solution was in the white opaque state at 80° C. Next, the temperature control of the water bath was off while still stirred, so that the solution was slowly cooled down at room temperature. It took about 90 min for the temperature of the water bath to be cooled from 80° C. to 35° C. The solution, which was in the white opaque state at 80° C., turned into a slightly pale transparent state around at 72° C., and the transparency persisted until the temperature fell to around 62° C. From around 62° C., the solution started to become white opaque again, turning into a completely white opaque state at 58° C. This change of state was reversible: the similar change of state was observed when the temperature was gradually raised from room temperature.

3.2: Examination on Whether Phospholipid Alone or Cholesterol Alone can be Dissolved 75.9 mg of DPPC and 40 mg of cholesterol were separately weighed into glass vials, to each of which a mixture of 4 mL of 10 wt/vol % sucrose solution and 0.85 mL of t-BuOH was added; and similar experiments as those in 3.1 were conducted. Where DPPC alone was used, the aqueous solution was in the transparent state between 80° C. and 50° C., turning into a slightly pale transparent state at around 48° C. This state persisted until the temperature fell down to about 35° C., where the solution suddenly changed into a white opaque state. In contrast, where cholesterol alone was used, aggregates of cholesterol adhering to the vial wall were observed and the solution never became transparent at any temperature.

3.3 Examination of the t-BuOH Concentration 32.7 mg of DPPC and 17.2 mg of cholesterol were put together into glass vials. t-BuOH in volumes shown in the table below and 2 ml of 50% sucrose solution were mixed to the lipid mixture, and then pure water was added at a final volume of 10 m L. Thus solutions containing t-BuOH at various concentrations were prepared.

TABLE 1

| t-BuOH final concentration (vol %) | t-BuOH volume (mL) | 50% sucrose volume (mL) | Volume after addition of pure water (mL) |
|---|---|---|---|
| 10 | 1 | 2 | 10 |
| 12 | 1.2 | 2 | 10 |
| 14 | 1.4 | 2 | 10 |
| 16 | 1.6 | 2 | 10 |
| 18 | 1.8 | 2 | 10 |
| 20 | 2.0 | 2 | 10 |
| 22 | 2.2 | 2 | 10 |
| 24 | 2.4 | 2 | 10 |
| 26 | 2.6 | 2 | 10 |
| 28 | 2.8 | 2 | 10 |

Each vial was stirred in a water bath at 90° C. for 10 min, removed from the water bath, and then cooled with stirring at room temperature. After cooling, a part of the liposome suspensions was removed and diluted with PBS (or 10 wt/vol % sucrose solution). Particle size distributions were measured using the Zetasizer Nano ZS. The result is shown in the table below. Additionally, as an example, the particle size distribution chart of the liposome suspension prepared under the conditions of the t-BuOH concentration of 16 vol % is shown in FIG. 1. In Table 2, the asterisk (*) indicates heterogeneous particles which do not meet the quality standard for particle diameter measurement established by Malvern.

TABLE 2

| t-BuOH concentration (vol %) | Z-Average (d · nm) | PDI | Result quality |
|---|---|---|---|
| 10 | 2338 | 1.000 | * |
| 12 | 442 | 0.196 | Good |
| 14 | 651 | 0.194 | Good |
| 16 | 498 | 0.195 | Good |
| 18 | 394 | 0.130 | Good |
| 20 | 1589 | 0.644 | * |
| 22 | 1324 | 0.529 | * |
| 24 | 1463 | 0.747 | * |
| 26 | 1160 | 0.708 | * |
| 28 | 1010 | 0.630 | * |

As shown in Table 2 and FIG. 1, liposomes extremely uniform in particle diameter could be successfully produced particularly in the t-BuOH concentration of 12 to 18 vol %.

3.4: Examination of the Concentrations of 1-propanol, 2-propanol, 2-butoxyethanol, etc.

Preferred concentration ranges of the water-miscible solvents were examined by the same method as that in 3.3., except that t-BuOH was replaced by 1-propanol, 2-propanol, or 2-butoxyethanol. The results are shown in the three tables below.

TABLE 3

| 1-propanol concentration (vol %) | Z-Average (d · nm) | PDI | Result quality |
|---|---|---|---|
| 3 | 1107 | 0.759 | * |
| 4 | 2596 | 0.515 | * |
| 5 | 943.6 | 0.426 | Good |
| 7 | 349.1 | 0.222 | Good |
| 11 | 373.4 | 0.217 | Good |
| 15 | 949.1 | 0.302 | Good |
| 18 | 1130 | 0.206 | Good |
| 19 | 929.1 | 0.064 | Good |
| 20 | 1897 | 0.185 | * |

TABLE 4

| 2-propanol concentration (vol %) | Z-Average (d · nm) | PDI | Result quality |
|---|---|---|---|
| 12 | 10.49 | 0.608 | * |
| 13 | 355.7 | 0.2 | Good |
| 14 | 360.2 | 0.22 | Good |
| 18 | 551.3 | 0.29 | Good |
| 20 | 951.3 | 0.246 | Good |
| 24 | 1482 | 0.168 | Good |
| 26 | 1404 | 0.258 | Good |
| 27 | 1749 | 0.463 | * |
| 29 | 1303 | 0.527 | * |

TABLE 5

| 2-butoxyethanol concentration (vol %) | Z-Average (d · nm) | PDI | Result quality |
|---|---|---|---|
| 4 | 914.4 | 0.843 | * |
| 5 | 1287 | 0.440 | * |
| 6 | 1308 | 0.121 | Good |
| 7 | 930.7 | 0.187 | Good |
| 8 | 1382 | 0.103 | Good |

TABLE 5-continued

| 2-butoxyethanol concentration (vol %) | Z-Average (d · nm) | PDI | Result quality |
|---|---|---|---|
| 9 | 705.9 | 0.310 | Good |
| 10 | 1309 | 0.298 | * |
| 11 | 2898 | 1.000 | * |

As shown in Tables 3 to 5, liposomes extremely uniform in particle diameter could be successfully produced in the range of 5 to 19 vol % for 1-propanol, in the range of 13 to 26 vol % for 2-propanol, and in the range of 6 to 9 vol % for 2-butoxyethanol.

3.5: Examination in Terms of Changes in the Lipid Composition (1)

To individual vials, 75.9 mg of DPPC, 40.0 mg of cholesterol, and 14.3 mg of stearylamine or 0.772 mg of DPPG were added. Subsequently, 10 wt/vol % sucrose solution containing 17 vol % t-BuOH, 10 wt/vol % sucrose solution containing 17 vol % 1-propanol, 10 wt/vol % sucrose solution containing 25 vol % 2-propanol, or 10 wt/vol % sucrose solution containing 8 vol % 2-butoxyethanol was added to each vial at a volume of 4.85 mL each. Each vial was stirred in a water bath at 70° C. for 30 min, and then cooled with stirring at room temperature. After cooling, apart of the liposome suspension was removed and diluted with PBS. Particle size distributions were measured using the Zetasizer Nano ZS. The results are shown in Tables 6 and 7 as well as FIGS. 2 and 3. Furthermore, the liposome suspensions were diluted with PBS, liposomes were precipitated by centrifugation, and the supernatant was replaced by PBS (i.e. washing by centrifugation). By repeating washing by centrifugation 3 times, the solutions dispersing liposomes were replaced by PBS, and the water-miscible organic solvent and the sucrose outside liposomes were removed. Then, after quantification of the cholesterol in the liposome suspensions, the content of the sugar (sucrose) which was used for the preparation of the liposomes and was encapsulated inside the liposomes was measured by the phenol-sulfuric acid method. The ratios of sugar encapsulation were obtained by the formula: (ratio of sugar concentration to cholesterol concentration after centrifugal washing)/(ratio of the sugar concentration to cholesterol concentration before washing by centrifugation).

TABLE 6

Result with use of DPPC, cholesterol, and stearylamine

| Solvent | Average particle diameter [nm] | PDI | Sugar encapsulation ratio |
|---|---|---|---|
| 1-propanol | 248 | 0.059 | 0.188 |
| 2-propanol | 699 | 0.339 | 0.193 |
| 2-butoxyethanol | 493 | 0.100 | 0.264 |
| t-BuOH | 443 | 0.074 | 0.309 |

TABLE 7

Result with use of DPPC, cholesterol, and DPPG

| Solvent | Average particle diameter [nm] | PDI | Sugar encapsulation ratio |
|---|---|---|---|
| 1-propanol | 165 | 0.066 | 0.212 |
| 2-propanol | 185 | 0.171 | 0.313 |

TABLE 7-continued

Result with use of DPPC, cholesterol, and DPPG

| Solvent | Average particle diameter [nm] | PDI | Sugar encapsulation ratio |
|---|---|---|---|
| 2-butoxyethanol | 228 | 0.228 | 0.396 |
| t-BuOH | 191 | 0.235 | 0.435 |

As shown in Tables 6 and 7 as well as FIGS. 2 and 3, where t-BuOH or 2-butoxyethanol is used as the water-miscible organic solvent, almost the same particle diameter and sugar encapsulation ratio were obtained. In particular, where t-BuOH is used, sucrose (sugar) used for the liposome preparation was encapsulated into liposomes at an extremely high ratio of 40% or more. This strongly suggests that, by dissolving a substance to be encapsulated into the solution for liposome preparation, the substance is encapsulated in the liposome at an extremely high ratio, as with sucrose.

3.6: Examination in Terms of Changes in the Lipid Composition (2)

Mixture (1) was prepared by putting 76 mg of DPPC and 40 mg of cholesterol into a vial and then adding 4 mL of 10 wt/vol % sucrose solution and 0.85 mL of t-BuOH. Mixtures (2) and (3) were prepared by putting 76 mg of DPPC, 40 mg and 30 mg of cholesterol, respectively, and 0.77 mg of DPPG into vials and then adding 4 mL of 10 wt/vol % sucrose solution and 0.85 mL of t-BuOH. Mixture (4) was prepared by putting 67.7 mg of DPPC, 40.6 mg of cholesterol, 9.1 mg of DPPE, and 7.3 mg of DCP into a vial and then adding 4 mL of 10 wt/vol % sucrose solution and 0.85 mL of t-BuOH. Mixture (5) was prepared by putting 76 mg of DPPC, 40 mg of cholesterol, and 14.3 mg of SA into a vial and then adding 4 mL of 10 wt/vol % sucrose solution and 0.85 mL of t-BuOH. Mixture (6) was prepared by putting 76 mg of HSPC and 40 mg of cholesterol into a vial and then adding 4 mL of 10 wt/vol % sucrose solution and 0.85 mL of t-BuOH. Each vial was stirred in a water bath at 70° C. for 30 min, and then cooled with stirring at room temperature. After cooling, an aliquot of the liposome suspension was removed and diluted with PBS. Particle size distributions were measured to obtain average liposome particle size using the Zetasizer Nano ZS. The result is shown in the table below.

TABLE 8

| Mixture | Lipid composition (molar ratio) | Average particle size of liposomes (Z-Average, nm) |
|---|---|---|
| (1) | DPPC:Chol. = 1:1 | 490 |
| (2) | DPPC:Chol.:DPPG = 1:1:0.01 | 260 |
| (3) | DPPC:Chol.:DPPG = 1:0.75:0.01 | 420 |
| (4) | DPPC:Chol.:DPPE:DCP = 41:47:6:6 | 180 |
| (5) | DPPC:Chol.:SA = 1:1:0.51 | 364 |
| (6) | HSPC:Chol. = 76:40 (weight ratio) | 279 |

The result revealed that the average particle size of the produced liposomes varied depending on the lipid composition.

3.7: Examination of Cooling Rate

A solution containing 17.5 vol % t-BuOH was prepared by adding 1.75 mL of t-BuOH and 2 mL of 50% sucrose aqueous solution, and then adding pure water to make its final volume 10 mL. Next, 32.7 mg of DPPC and 17.2 mg of cholesterol were put into glass vials. 2 mL of the solution containing 17.5 vol % t-BuOH was added to the lipid mixture. The vials were stirred for 10 min in a water bath maintained at 70° C. Subsequently, the vials were cooled at a cooling of 1° C./min by transferring them to water baths with the temperature at 50° C., 40° C., and 30° C. When the temperatures of the vials became 50° C., 40° C., and 30° C., aliquots of the liposome suspension were removed, diluted with PBS, and subjected to particle size distribution measurement using the Zetasizer Nano ZS. Further, for comparison, a vial containing the same lipid mixture as the above, to which 2 mL of the solution containing 17.5 vol % t-BuOH was added, was stirred for 10 min in a water bath maintained at 80° C. With still stirring, temperature control of the water bath temperature was turned off and the vial was slowly cooled down at room temperature. Cooling from 80° C. to 35° C. required 90 min (cooling rate: 0.5° C./min). When the temperature of the vial became 35° C., an aliquot of the liposome suspension was removed, diluted with PBS, and subjected to particle size distribution measurement using The Zetasizer Nano ZS. The result is shown in the table below.

TABLE 9

| Temperature (° C.) | Z-Average (d · nm) | PDI | Result quality |
|---|---|---|---|
| 50 (Rapid cooling) | 527.9 | 0.240 | Good |
| 40 (Rapid cooling) | 516.8 | 0.217 | Good |
| 30 (Rapid cooling) | 517.1 | 0.217 | Good |
| 35 (Slow cooling) | 1014 | 0.577 | * |

As shown in Table 9, the liposomes in the liposome suspension rapidly cooled down to 50° C., 40° C., and 30° C. were highly uniform in particle diameter with an average particle diameter of about 500 nm. The uniformity of the liposomes in the liposome suspension treated by slow cooling were low, compared with the aforementioned three groups of liposomes.

3.8: Investigation of Optimum Temperature of Liposome-Forming Tank 330 Shown in FIG. 1

In a thermostatic bath being maintained at 75° C., 7.8 g of phospholipid (NC-61, NOF Corporation), 4.1 g of cholesterol (Nippon Fine Chemical Co., Ltd., Japanese Pharmacopeia), and 80 mL of t-butanol (Wako Pure Chemical Industries, Ltd.) were mixed by stirring to completely dissolve the lipid. The resulting lipid solution was cooled to room temperature, and 420 mL of a 10% sucrose solution was added thereto. The resulting mixture was heated again in a thermostatic bath to dissolve the lipid component, followed by stirring at 75° C. for 30 min. The solution was cooled to room temperature to produce a preliposome solution.

The preliposome solution was treated to form liposomes in the liposome-producing apparatus 1 shown in FIG. 1. The temperatures of water serving as the heat medium for the lipid-dissolving tank 310, the liposome-forming tank 330, and the cooling tank 340, as well as the lengths and the inner diameters of the microtubes, in the liposome-producing apparatus 1 are shown in the following table. The pump 6 shown in FIG. 1 was UNIflows uf.7020PSB2. The flow rate of the pump 6 was set to 5 mL/min.

TABLE 10

|  | Temperature | Tube length | Tube inner diameter |
|---|---|---|---|
| Lipid-dissolving tank | 72° C. | 5 m | 1 mm |
| Liposome-forming tank | 40~70° C. | 5 m | 1 mm |
| Cooling tank | 4° C. | 5 m | 1 mm |

Figure 10:
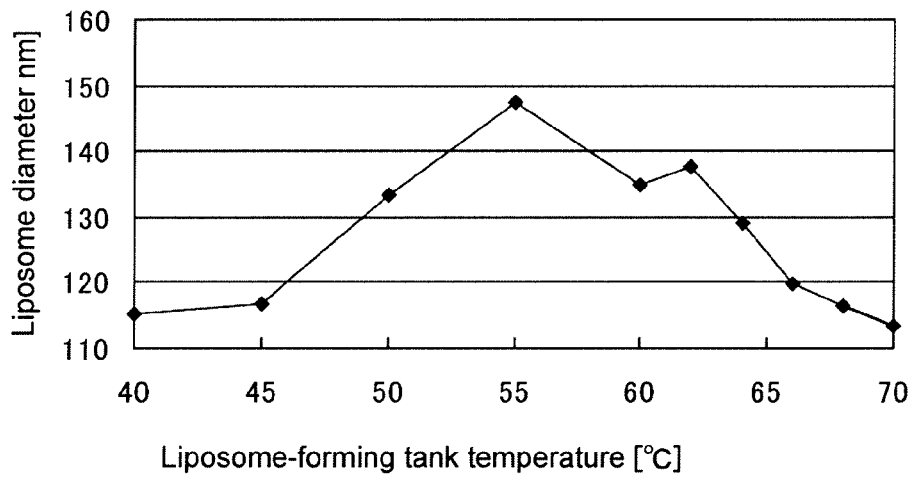
FIG. 10 is a graph showing a relationship between the temperature of a heat medium of a liposome-forming tank 330 in a liposome-producing apparatus 1 and the liposome diameter, which has been investigated in an example of the present invention.

Variations in diameter of liposomes due to a transition of the temperature (40, 45, 50, 55, 60, 62, 64, 66, 68, or 70° C.) of the heat medium of the liposome-forming tank 330 were investigated. The diameters were measured with a particle-size distribution analyzer (Malvern Instruments Ltd., ZETA SIZER Nano-ZS). As a result, liposomes having uniform diameters could be formed with good reproducibility. As shown in FIG. 10, the diameters of liposomes become the maximum at about 55° C., and there is a specific temperature range for making liposomes grow in size.

3.9: Investigation of Retention Time in Liposome-Forming Tank 330 Shown in FIG. 1

Figure 11:
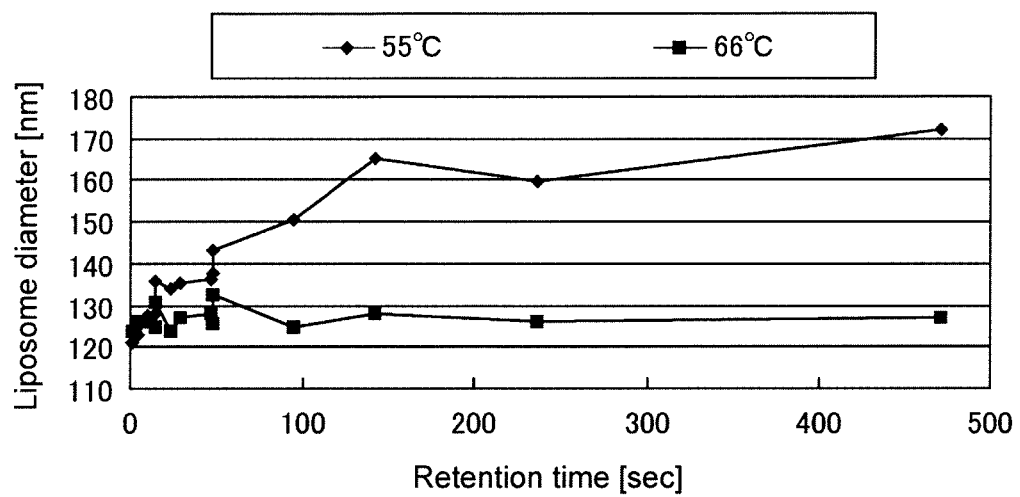
FIG. 11 is a graph showing a relationship between the retention time in a heat medium of a liposome-forming tank 330 in a liposome-producing apparatus 1 and the liposome diameter, which has been investigated in an example of the present invention.

The temperatures of water serving as the heat medium and the lengths and the inner diameters of the microtubes of the lipid-dissolving tank 310, the liposome-forming tank 330, and the cooling tank 340, as well as the flow rates of the pump 6, in the liposome-producing apparatus 1 were set as shown in the following table. The liposome solution prepared in Example 3.8 was treated to form liposomes in the liposome-producing apparatus 1. The diameters of the liposomes were measured similarly to Example 3.8 to investigate a relationship between the retention time in the liposome-forming tank 330 and the liposome diameter. The retention time in the liposome-forming tank 330 was calculated by the expression: (retention time)=(internal volume of tube in liposome-forming tank)/(pump flow rate). FIG. 11 shows the results.

TABLE 11

|  | Temperature | Tube length | Tube inner diameter |
|---|---|---|---|
| Lipid-dissolving tank | 72° C. | 5 m | 1 mm |
| Liposome-forming tank | 55° C. or 66° C. | 0.3~10 m | 1 mm |
| Cooling tank | 4° C. | 5 m | 1 mm |

TABLE 12

| Flow rate (mL/min) | Tube length (m) | Retention time (sec) |
|---|---|---|
| 10 | 0.3 | 1.4 |
| 5 | 0.3 | 2.8 |
| 10 | 1 | 4.7 |
| 5 | 1 | 9.4 |
| 10 | 3 | 14.1 |
| 1 | 0.3 | 14.1 |
| 10 | 5 | 23.6 |
| 5 | 3 | 28.3 |
| 10 | 10 | 47.1 |
| 5 | 5 | 47.1 |
| 1 | 1 | 47.1 |
| 5 | 10 | 94.2 |
| 1 | 3 | 141.3 |
| 1 | 5 | 235.5 |
| 1 | 10 | 471.0 |

When the temperature of the liposome-forming tank 330 was set to 55° C., the diameters of liposomes could be increased by extending the retention time in the liposome-forming tank 330. On the other hand, when the temperature of the liposome-forming tank 330 was set to 60° C., the diameters of liposomes did not change at the retention time of 100 sec or more. Thus, the liposome diameters can be controlled by using the liposome-producing apparatus 1 of the present invention and controlling the temperature of the liposome-forming tank 330 and the retention time therein.

INDUSTRIAL APPLICABILITY

The liposome producing apparatus according to the present invention can be applied to, for example, production of DDS, microcapsules for cosmetics, and the like.

REFERENCE SIGNS LIST

1 liposome-producing apparatus
2 housing for dissolution (included in dissolving zone)
3 first housing for cooling (included in first cooling zone)
8 second housing for cooling (included in second cooling zone)
20, 21, 26, 30, 31, 80 tube (solution sending channel)
22 sterilization filter
23a, 23b, 24, 25, 27, 33, 34, 35, 36, 81, 85 T-shaped joint (solution sending channel)
32, 82 sterilization filter
100 preliposome-forming device
130 solution-sending pump (encapsulation material feeder)
140 encapsulation material container (encapsulation material feeder)
200 UF device (ultrafiltration device)
301 container
304 liposome-collecting container
310 lipid-dissolving tank
320 sterilization filter
330 liposome-forming tank
340 cooling tank
312, 332, 342 thermostatic bath

The invention claimed is:
1. A liposome-producing apparatus comprising:
a dissolving zone for preparing a lipid solution by heating a mixture containing one or more lipids and an aqueous solution containing a water-miscible organic solvent in the microtube to dissolve the lipid(s) in the aqueous solution;
a microtube comprising a channel in which the lipid solution flows;
a housing for housing the microtube;
a cooling unit for cooling the lipid solution in the microtube in the housing to a liposome-forming temperature, and
a sterilization filter for sterilizing the lipid solution.
2. The liposome-producing apparatus according to claim 1, wherein the dissolving zone includes a microtube having a channel in which the mixture flows; and the microtube of the dissolving zone and the microtube in the housing are connected to each other.
3. The liposome-producing apparatus according to claim 1, the apparatus further comprising a preliposome-forming device for forming liposomes by heating the mixture, before heating the mixture at the dissolving zone, to dissolve the lipid or lipids in the aqueous solution and then cooling the resulting solution to a temperature lower than the dissolving temperature.
4. The liposome-producing apparatus according to claim 1, the apparatus further comprising an encapsulation material feeder for supplying both the lipid solution and a material to be encapsulated inside liposomes to the microtube in the housing.

5. The liposome-producing apparatus according to claim 1, the apparatus further comprising a cooling zone for further cooling the solution containing the liposomes formed by cooling with the cooling unit.

6. The liposome-producing apparatus according to claim 1, the apparatus further comprising an ultrafiltration device for concentrating the solution containing the liposomes formed by cooling with the cooling unit by removing at least the watermiscible organic solvent from the solution.

7. The liposome-producing apparatus according to claim 1, wherein the microtube has a coiled shaped.

8. The liposome-producing apparatus according to claim 1, wherein the cooling unit contains gas only.

9. The liposome-producing apparatus according to claim 1, wherein the cooling unit contains liquid only.

\* \* \* \* \*